(12) United States Patent
Wilkins

(10) Patent No.: US 12,371,650 B2
(45) Date of Patent: Jul. 29, 2025

(54) METHOD AND SYSTEM FOR PROVIDING BUFFER SOLUTIONS

(71) Applicant: LONZA LTD, Visp (CH)

(72) Inventor: Tristan Wilkins, Newmarket, NH (US)

(73) Assignee: LONZA LTD, Visp (CH)

( * ) Notice: Subject to any disclaimer, the term of this patent is extended or adjusted under 35 U.S.C. 154(b) by 0 days.

(21) Appl. No.: 18/538,702

(22) Filed: Dec. 13, 2023

(65) Prior Publication Data

US 2024/0132830 A1     Apr. 25, 2024

Related U.S. Application Data

(63) Continuation of application No. 16/876,498, filed on May 18, 2020, now Pat. No. 11,898,137, which is a continuation of application No. 15/667,387, filed on Aug. 2, 2017, now Pat. No. 10,669,518.

(60) Provisional application No. 62/370,041, filed on Aug. 2, 2016.

(51) Int. Cl.
| | |
|---|---|
| *B67D 7/00* | (2010.01) |
| *C12M 1/00* | (2006.01) |
| *C12M 1/12* | (2006.01) |
| *C12M 1/34* | (2006.01) |
| *C12M 3/00* | (2006.01) |
| *B67D 7/02* | (2010.01) |

(52) U.S. Cl.
CPC ............ *C12M 41/32* (2013.01); *C12M 23/44* (2013.01); *C12M 29/00* (2013.01); *C12M 37/00* (2013.01); *C12M 41/36* (2013.01); *C12M 43/00* (2013.01); *B67D 7/0294* (2013.01)

(58) Field of Classification Search
CPC ...... C12M 23/44; C12M 41/32; B67D 7/0294
See application file for complete search history.

(56) References Cited

U.S. PATENT DOCUMENTS

| | | |
|---|---|---|
| 5,272,071 A | 12/1993 | Chappel |
| 5,474,411 A | 12/1995 | Schoenfeld et al. |
| 5,633,162 A | 5/1997 | Keen et al. |
| (Continued) | | |

FOREIGN PATENT DOCUMENTS

| | | |
|---|---|---|
| CN | 1654282 A | 8/2005 |
| CN | 101981600 A | 2/2011 |
| (Continued) | | |

OTHER PUBLICATIONS

Norris, "Method for Evaluating Bio-Container Transportation Applications," BioProcess International. Jul. 1, 2008.

(Continued)

*Primary Examiner* — Anshu Bhatia
(74) *Attorney, Agent, or Firm* — MEDLER FERRO WOODHOUSE & MILLS PLLC

(57) ABSTRACT

A method for delivering a processing solution includes providing a concentrated processing solution in a bioprocess container, the concentrated processing solution being produced at a first site. The method also includes combining the concentrated processing solution with a biopolymer containing solution produced in a bioreactor at a second site different from the first site. In some embodiments, the processing solution is a buffer for processing products of cells cultured in a bioreactor. A system and a pharmaceutical production facility for carrying out the method is also provided.

10 Claims, 14 Drawing Sheets

(56) References Cited

U.S. PATENT DOCUMENTS

| | | | |
|---|---|---|---|
| 5,656,491 | A | 8/1997 | Cassani et al. |
| 6,326,193 | B1 | 12/2001 | Liu et al. |
| 6,393,775 | B1 | 5/2002 | Staschik |
| 6,703,199 | B1 | 3/2004 | Koide |
| 7,515,994 | B2 | 4/2009 | Bellafiore et al. |
| 7,629,167 | B2 | 12/2009 | Hodge et al. |
| 8,298,054 | B2 | 10/2012 | Hodge et al. |
| 9,158,345 | B1 | 10/2015 | Rice et al. |
| 9,946,902 | B2 | 4/2018 | Nyffeler et al. |
| 2001/0047628 | A1 | 12/2001 | Mouton et al. |
| 2002/0189173 | A1 | 12/2002 | Staschik |
| 2004/0079691 | A1 | 4/2004 | Jowett |
| 2005/0193643 | A1* | 9/2005 | Pettus .................... F24F 3/167 52/79.1 |
| 2005/0205658 | A1 | 9/2005 | Baker et al. |
| 2005/0235581 | A1 | 10/2005 | Cohen et al. |
| 2009/0037031 | A1 | 2/2009 | George et al. |
| 2009/0300998 | A1 | 12/2009 | Ablett |
| 2009/0305626 | A1 | 12/2009 | Hope |
| 2011/0240497 | A1 | 10/2011 | Dechene et al. |
| 2011/0258837 | A1 | 10/2011 | Scannon et al. |
| 2012/0077429 | A1 | 3/2012 | Wernimont et al. |
| 2013/0067721 | A1 | 3/2013 | Scannon et al. |
| 2013/0109291 | A1 | 5/2013 | Holtz et al. |
| 2013/0164400 | A1* | 6/2013 | Knopov ............... A61K 9/4833 425/5 |
| 2013/0233532 | A1 | 9/2013 | Imwalle et al. |
| 2013/0280797 | A1 | 10/2013 | Rao et al. |
| 2014/0335566 | A1 | 11/2014 | Guerini et al. |
| 2015/0036266 | A1 | 2/2015 | Emert et al. |
| 2015/0101264 | A1 | 4/2015 | Jornitz |
| 2016/0105988 | A1 | 4/2016 | Englert et al. |
| 2016/0312485 | A1 | 10/2016 | Wilson et al. |
| 2016/0376784 | A1 | 12/2016 | Timur |
| 2017/0008752 | A1* | 1/2017 | Tuohey ................ F16K 31/126 |

FOREIGN PATENT DOCUMENTS

| | | |
|---|---|---|
| DE | 9014558 U1 | 1/1991 |
| EP | 2103548 | 9/2009 |
| JP | H04-368568 A | 12/1992 |
| JP | 2008-041102 A | 2/2008 |
| JP | 2011-509685 A | 3/2011 |
| JP | 2011-518370 A | 6/2011 |
| JP | 2012513649 A | 6/2012 |
| WO | 0129058 | 4/2001 |
| WO | 0196584 | 12/2001 |
| WO | 2015/117883 A1 | 8/2015 |
| WO | 2015117883 | 8/2015 |

OTHER PUBLICATIONS

Fritchman et al. "Strategic Outsourcing of Media Design and Cell Culture Media Manufacturing" Biopharm International (2009) vol. 22, No. 9, pp. 18-19.

Haigney "Integrating Single-Use Systems in Pharma Manufacturing" Pharmatech (2016) vol. 40, No. 6, pp. 1-5; Retrieved from the Internet at http://www.pharmtech.com/inteoratina-single-use-systems-aharma-manufacturing; Retrieved on Oct. 30, 2017.

International Search Report and Written Opinion for International Application No. PCT/US2017/043768 dated Nov. 13, 2017.

International Search Report and Written Opinion for International Application No. PCT/US2017/045162 dated Nov. 17, 2017.

Shukla et al. "Single-use disposable technologies for biopharmaceutical manufacturing" Trends in Biotechnology (2013) vol. 31, No. 3, pp. 147-154.

All Foreign Patent Documents and Non-Patent Literature is provided in priority U.S. Appl. No. 15/667,387.

Haigney, "Integrating Single-Use Systems in Pharma Manufacturing," Pharmaceutical Technology 40(6), pp. 42-44 (Jun. 2, 2016).

Patterson, "Automated In-Line Dilution—A QbD Manufacturing Method", Journal of GXP Compliance, vol. 12, pp. 20-33, Nov. 5, 2008.

* cited by examiner

METHOD AND SYSTEM FOR PROVIDING BUFFER SOLUTIONS

CROSS REFERENCE TO RELATED APPLICATIONS

This application is a continuation of U.S. patent application Ser. No. 16/876,498, filed on May 18, 2020 which is a divisional of U.S. patent application Ser. No. 15/667,387, filed Aug. 2, 2017, which claims the benefit of priority to U.S. Provisional Patent Application Ser. No. 62/370,041 filed on Aug. 2, 2016, the disclosures of which are hereby incorporated herein by reference in their entireties for all purposes.

FIELD OF THE INVENTION

The disclosure relates to solutions, e.g., buffers, for processing products of cells cultured in a bioreactor.

BACKGROUND

Bioreactors are used to produce large quantities of desired bioproducts. After growth of cells in a bioreactor to produce the bioproduct, subsequent steps are performed to isolate and concentrate the bioproduct. These processing steps can require large volumes of expensive processing solutions to maintain sterility and ensure that the bioproduct retains its activity. There is a need for a more cost effective way to produce solutions for processing bioproducts.

SUMMARY

An aspect of the present disclosure is related to a system for delivering a processing solution, the system comprising a bioprocess container containing a concentrated processing solution, the concentrated processing solution produced at a first site; a processing area having at least one processing unit at a second site different from the first site; and a pipe connecting the bioprocess container to the at least one processing unit, the pipe having a valve to allow the concentrated processing solution to flow from the bioprocess container to the at least one processing unit to combine the concentrated processing solution with a biopolymer-containing solution produced in the at least one processing unit, wherein the processing solution is at least one of a buffer and media.

In some embodiments, the system further includes a controller connected to the at least one processing unit, wherein the concentrated processing solution is provided based on a determination by the controller that the processing solution is required when the determination is communicated from the second site to the first site.

In some embodiments, the system is configured to dilute the concentrated processing solution prior to combining with the biopolymer containing solution.

In some embodiments, the processing solution is Tris, Tris-Base, Tricine, HEPES, MOPS, PIPES, TAPS, bicine, BES, TES, cacodylate, MES, acetate, MKP, ADA, ACES, glycinamide, acetamidoglycine, acetic acid, citric acid, glycine, glycine glycinate, sodium phosphate, ethanol, hydrochloric acid, sodium hydroxide, guanidinium chloride, guanidine hydrochloride, sodium chloride, and/or a combination of any of these.

In some embodiments, the bioprocess container includes an inner layer for contacting the processing solution and an outer layer configured to support the inner layer.

In some embodiments, the inner layer is polyethylene, and the outer layer is a blend of polyethylene, EVOH, nylon, and PVDC.

In some embodiments the system includes a controller configured to determine a bioburden of the processing solution.

In some embodiments, the system includes a dilution liquid supply, wherein a concentrated processing solution from the bioprocess container and water and/or buffer from the dilution liquid supply are added to an inlet of an inline processing solution dilution system to result in a diluted processing solution.

In some embodiments, the at least one processing unit further includes a plurality of bioreactors.

In some embodiments, the system includes a plurality of bioprocess containers.

In some embodiments, the processing solution is a buffer.

Another aspect of the present disclosure is related to a method for delivering a processing solution, the method comprising providing a concentrated processing solution in a bioprocess container, the concentrated processing solution being produced at a first site; and combining the concentrated processing solution with a biopolymer-containing solution produced in a bioreactor at a second site different from the first site, wherein the processing solution is at least one of a buffer and media.

In some embodiments, the concentrated processing solution is provided based on a determination that the concentrated processing solution is required and the determination is communicated from the second site to the first site.

In some embodiments, the method includes diluting the concentrated processing solution prior to combining with the biopolymer containing solution.

In some embodiments, the processing solution is Tris, Tris-Base, Tricine, HEPES, MOPS, PIPES, TAPS, bicine, BES, TES, cacodylate, MES, acetate, MKP, ADA, ACES, glycinamide, acetamidoglycine, acetic acid, citric acid, glycine, glycine glycinate, sodium phosphate, ethanol, hydrochloric acid, sodium hydroxide, guanidinium chloride, guanidine hydrochloride, sodium chloride, and/or a combination of any of these.

In some embodiments, the bioprocess container comprises an inner layer for product contact and an outer layer configured to support the inner layer.

In some embodiments, the inner layer is polyethylene, and the outer layer is a blend of polyethylene, EVOH, nylon, and PVDC.

In some embodiments, the method includes determining a bioburden of the processing solution. In some embodiments, the bioburden is determined in a rapid detection assay.

In some embodiments, the method includes adding concentrated processing solution from the bioprocess container and water and/or buffer from a dilution liquid supply to an inlet of an inline processing solution dilution system to result in a diluted processing solution.

In some embodiments, the method includes transporting the bioprocess container containing the processing solution from the first site to the second site.

In some embodiments, the method includes feeding bioprocessing solution through an outlet in the bioprocess container to facilitate purification of the biopolymer.

Another aspect of the present disclosure is related to a pharmaceutical production facility comprising a buffer storage area capable of receiving at least one bioprocess container configured to contain a concentrated processing solution; a processing area having at least one processing unit; a wall separating the buffer storage area from the processing area; and at least one pipe having a first end in the buffer storage area and a second end in the processing area, the first end configured to connect to at least one bioprocess container of the at least one bioprocess container, and the second end configured to connect to at least one processing unit of the at least one processing unit.

In some embodiments, the at least one pipe has a valve.

In some embodiments, the at least one bioprocess container includes an inner layer for contacting the processing solution and an outer layer configured to support the inner layer.

In some embodiments, the pharmaceutical production facility of claim, further includes a platform in the buffer storage area, the platform being configured to support the at least one bioprocess container, the at least one bioprocess container including a plurality of bioprocess containers, the platform having a first level configured to support at least one bioprocess container of the plurality of bioprocess containers and a second level configured to support at least one bioprocess container of the plurality of bioprocess containers, wherein the platform is configured to allow a user to place a bioprocess container of the plurality of bioprocess containers onto the platform using a forklift, and the platform being configured to allow a user to remove the respective bioprocess container from the platform using the forklift.

In some embodiments, the pharmaceutical production facility further includes a plurality of inlets spaced apart along the platform, each inlet being connected to the at least one pipe, and each inlet being configured to be connected to an outlet of a bioprocess container of the plurality of bioprocess containers.

In some embodiments, the processing area is configured as a cleanroom environment.

In one aspect, the invention provides a method, e.g., a method of delivering a bioreactor processing solution or a method of forming a biopolymer-containing solution. The method includes providing (e.g., receiving) a concentrated processing solution; combining the concentrated processing solution with a biopolymer-containing solution produced in a bioreactor, e.g., to form a biopolymer-containing solution.

In embodiments, the concentrated processing solution is provided in a unit of at least 20 liters, of about 20 to 2000 liters, e.g., 75, 100, 125, 250, 500, 1000, 1250, 1500, 1750, 1825, 1900, or 2000 liters.

In embodiments, the biopolymer containing solution comprises a biopolymer from tables entitled "Therapeutic Products and "Exemplary Products, e.g., Bispecific Molecules", below.

In embodiments, the biopolymer is made from a Chinese hamster ovary (CHO) cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1SV GS.

In embodiments, the processing solution is provided in one or more bioprocess containers.

In embodiments, the processing solution is provided in one or more bioprocess containers and is used for a single dilution.

In embodiments, the method comprises providing a value for the parameter, and optionally, comparing the value to a reference.

In embodiments, the evaluation is performed at a first site and the bioreactor is located at a second site.

In embodiments, the evaluation is performed at the site of the bioreactor.

In embodiments, the method comprises diluting the concentrated processing solution prior to combining with the biopolymer containing solution.

In embodiments, the processing solution is shipped or produced at a first site and the bioreactor is located at a second site.

In embodiments, the processing solution comprises a buffer, e.g., Tris, Tricine, HEPES, MOPS, PIPES, TAPS, bicine, BES, TES, cacodylate, MES, acetate, MKP, ADA, ACES, glycinamide and acetamidoglycine or acetic acid or similar In embodiments, the bioprocess container comprises an inner layer for product contact and an outer layer.

In embodiments, the inner layer is polyethylene.

In embodiments, the outer layer is a blend of polyethylene, EVOH, nylon, and/or PVDC.

In some embodiments, the method includes determining the bioburden of the processing solution.

In embodiments, the method comprises adding concentrated bioprocessing solution (concentrated processing solution) from a processing solution supply and water or buffer from the water/buffer supply to an inlet of an inline bioprocessing solution dilution system to result in diluted bioprocessing solution.

In embodiments, the method comprises feeding bioprocessing solution through an outlet in the bioprocess container to facilitate purification of the biopolymer.

Also provided by the invention is a system for delivering a bioprocessing solution. The system includes providing a concentrated processing solution produced at a first site and combining the concentrated biopolymer-containing solution with a biopolymer-containing solution produced in a bioreactor at a second site.

In embodiments, the concentrated bioprocessing solution is provided based on a determination that it is required and the determination is communicated from the second site to the first site.

Among the advantages of the invention is the ability to decouple production of a downstream processing solution from the manufacture of a biologic in a bioreactor. This, in combination of the use of buffer concentrates stored in bioprocess containers ("BPC"s aka buffer bags, or totes) allows for production of process intermediates to be prepared at a location remote to the biologics production. This reduces manufacturing costs. The extended stability time allows for review and release of GMP paperwork. As such, in process intermediates impacted by a GMP error or failed quality test can be rejected, therefore removing risk to the biologics production.

DETAILED DESCRIPTION

The invention provides cost-effective processing solutions for concentrating and purifying biologic products of large scale expression vessels, including bioreactors.

Biologics manufacturing typically include two main manufacturing stages. The first is a biologic product production stage, in which a biologic, typically a biopolymer such as a polypeptide or protein, is produced. The biopolymers are typically synthesized using microbial fermentation, biotransformation or mammalian cell culture. Bioreactor expression systems are disclosed in, e.g., U.S. 2011-0312087 A1.

The second step includes purifying the biologic product, in which the product is separated from impurities e.g. cellular debris, unwanted biopolymers, DNA media components and catabolytes. The second step can require large volumes of a biocompatible solution that preserves to the extent possible the desired activity of the biologic and is otherwise biocompatible with the biologic in order to selectively remove impurities a number of downstream processing stages (unit operations) are executed. During these unit operations a number of technologies are used including size exclusion filtration, chromatography, pH inactivation, refolding, tangential flow filtration, etc. To facilitate these unit operations a number of different aqueous solutions (buffers) are used which alter the physicochemical environment of the target molecule (e.g pH, conductivity).

Figure 1:
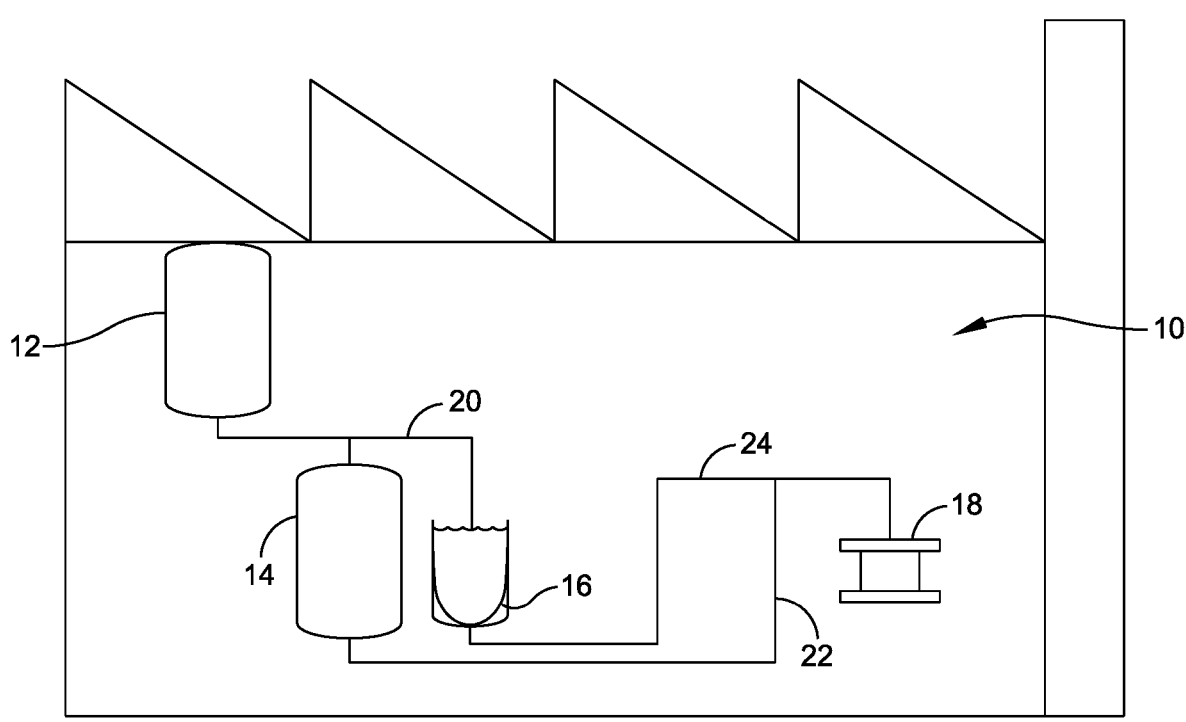
FIG. 1 is a schematic view of a prior art arrangement of a bioreactor preparation area.

A prior art arrangement of a bioreactor preparation area 10 is shown in FIG. 1. The buffer preparation area having a buffer preparation vessel 12 is in close physical proximity to a buffer storage area having a buffer hold tank 14 and a portable tote 16. The buffer preparation vessel 12 of the buffer preparation area is also in close physical proximity to a downstream processing area having a downstream processing unit, such as a chromatography column 18. A pipe 20 connects the buffer preparation vessel 12 to the buffer hold tank 14 and the portable tote 16. Another pipe 22 connects the buffer hold tank 14 to the downstream processing unit 18 in the downstream processing area. Yet another pipe 24 connects the portable tote 16 to the downstream processing unit 18 in the downstream processing area. This arrangement can be expensive and time consuming, which results in in-process material being used prior to completion of long lead testing and/or review and release of GMP records (batch records). Stockpiling of buffers occupies a large amount of GMP processing space.

Figure 2:
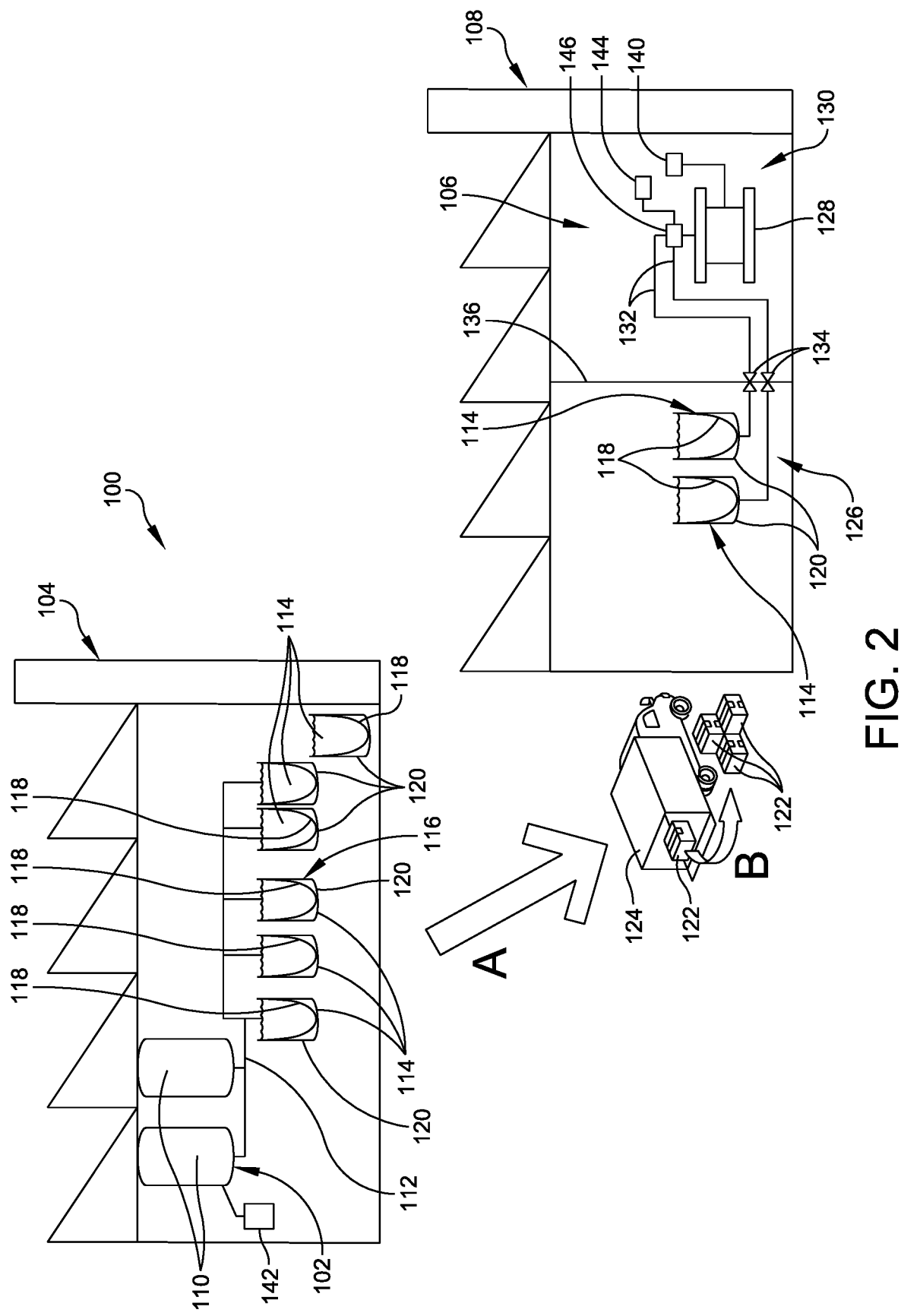
FIG. 2 is a schematic view of an embodiment of a buffer preparation arrangement according to the present disclosure.

In contrast, FIG. 2 shows an embodiment of a system 100 for delivering a processing solution according to the present disclosure. As shown, the system 100 includes a buffer preparation area 102 at first site 104, which is distinct from a downstream processing area 106 at a second site 108. In some embodiments, the first site 104 is a campus or building and the second site 108 is a campus or building distinct from the campus or building of the first site 104. While the buffer preparation area 102 and the downstream processing area 106 may be within one larger area, e.g., a factory or production site, no proximity is required as long as the concentrated solutions can be delivered to the downstream processing area without adversely affecting the stability or activity of the solution. Scheduling, formulation, and delivery of the solutions can be performed to prepare the solutions at or just before their intended time of use. In addition, the arrangement according to the disclosure allows for downstream processing solutions to be performed at a low value location, which can be preferable to preparing them at a high value location including the bioreactor. The arrangement also reduces storage space at the site of the bioreactor.

In FIG. 2, the buffer preparation area 102 includes at least two buffer preparation vessels, each indicated at 110. The buffer preparation vessels 110 are connected by at least one pipe (or at least one manifold) 112 to several storage tanks (or totes), each indicated at 114, in a buffer storage area 116. The buffer storage area 116 also includes at least one tote 114 that has been filled and is disconnected from the manifold so that it is ready to be transported to the second site 108.

The buffer preparation vessels 110 are useful for producing a processing solution. In some embodiments, the processing solution is a buffer such as Tris, Tricine, HEPES, MOPS, PIPES, TAPS, bicine, BES, TES, cacodylate, MES, acetate, MKP, ADA, ACES, glycinamide and acetamidoglycine or acetic acid or a buffer as shown in Tables 6-9.

Each tote 114 includes an inner layer or liner 118 for contacting the concentrated processing solution and an outer layer or body 120 that supports the inner layer. In some embodiments, the inner layer 118 is made of polyethylene. In some embodiments, the outer layer 120 is a blend of polyethylene, ethylene vinyl alcohol (EVOH), nylon, and polyvinylidene chloride (PVDC). In some embodiments, each tote 114 is made of plastic. In some embodiments, each tote 114 is capable of being sterilized by gamma radiation.

In some embodiments, each tote 114 is configured to ensure a shelf life of the processing solution contained within the tote for one month. In some embodiments, each tote 114 is configured to ensure a shelf life of the processing solution contained within the tote for three months. In some embodiments, each tote 114 is configured to ensure a shelf life of the processing solution contained within the tote for six months. In some embodiments, each tote 114 is configured to ensure a shelf life of the processing solution contained within the tote for one year.

In some embodiment each tote 114 has a volume of 1,000 liters (L). In some embodiments, each tote 114 has a rigid outer layer 120 that is capable of retaining a defined shape without external support on side walls of the tote 114.

At the buffer storage area 116, a user places one or more totes 114 on a shipping structure, such as a pallet. In one embodiment, a packaged tote supported on a pallet forms a shipping unit 122 is a 4 foot×4 foot×4 foot cube. The user places one or more shipping units 122 into a vehicle 124, such as a truck. The user drives the vehicle 124 from the buffer storage area 116 at a first facility (first site) 104 along the arrow A to a second facility (second site) 108 housing the downstream processing area 106.

At the second facility 108, the user unloads the shipping unit(s) 122 from the vehicle 124 along the arrow B. Then the user places the tote(s) 114 in a second buffer storage area 126 in the second site 108.

The second facility 108 includes at least one bioreactor 128 located in downstream processing area 130. In some embodiments, the downstream processing area 130 is a cleanroom. In the shown embodiment, two pipes, each indicated at 132, connect the totes (bioprocess containers)

114 located in the second buffer storage area 126 to the bioreactor 128 located in the downstream processing area 130. As shown, each pipe 132 includes a valve 134 that is positioned within or adjacent to a wall 136 of the downstream processing area 130, which separates the second buffer storage area 126 from the downstream processing area 130. The pipes 132 and the valves 134 in or adjacent the wall 136 allow the concentrated processing solution to flow from the bioprocess containers 114 to the bioreactor 128 to combine the concentrated processing solution with a biopolymer-containing solution produced in the bioreactor 128.

As mentioned above, the wall 136 separates the downstream processing area 130, which is formed as a cleanroom, from the second storage area 126, which is not necessarily a cleanroom. The valve 134 allows for a cleanroom compliant connection of the one or more totes 114 to the valve to minimize the risk of contaminating the bioreactor 128.

In some embodiments, each valve 134 depends from a ceiling at the second site 108.

When the processing solution is needed in the downstream processing area 106, the processing solution is pumped or otherwise moved from the totes 114 through the pipes 132 to the downstream processing unit 128 in the downstream processing area 106.

In some embodiments, the second site 108 includes a plurality of bioreactors 128 (or other downstream processing units) that are connectable to one or more totes 114. In some embodiments, only one tote 114 is used.

In some embodiments, the second site 108 includes at least one tote 114 that is currently connected to one or more bioreactors 128 as well as at least one tote 114 that is not yet connected to one or more bioreactors 128. This ensures that the user of the second site 104 has a backup supply of the processing solution contained in the totes 114.

The bioreactor 128 is connected to a controller 140. In some embodiments, the controller 140 is configured to determine that the processing solution contained in one or more totes 114 is required by the one or more bioreactors 128 at the second site 108. The controller 140 then communicates this determination to a controller 142 in the first site 104. This communication of the determination prevents a shortage of the processing solution at the second site 108.

In some embodiments, the controller 140 is configured to determine the bioburden of the processing solution. For example, the bioburden can be determined in a rapid detection assay. In some embodiments, the bioburden is determined in a Raman spectroscopy rapid detection assay.

The system 100 is configured to dilute the concentrated processing solution prior to combining with the biopolymer containing solution. This allows the system 100 to adjust the parameters such as the pH of the solution that is provided to the bioreactor 128. The system 100 includes a processing solution supply in the form of totes 114. The system 100 also includes a dilution liquid supply 144. In some embodiments, the dilution liquid can be water and/or a buffer. The concentrated processing solution from the totes 114 and water or buffer from the dilution liquid supply 144 are added to an inlet of an inline processing solution dilution system 146 along the pipes 132 to result in a diluted processing solution that is provided at an inlet of the bioreactor 128.

FIG. 2 shows only one bioreactor 128. More bioreactors may be included at the second site 108 without departing from the scope of the present disclosure. In some embodiments, the bioreactor(s) 128 in the second site 108 are useful for purification. In some embodiments, the bioreactor(s) 128 in the second site 108 include at least one chromatography column.

Figure 3:
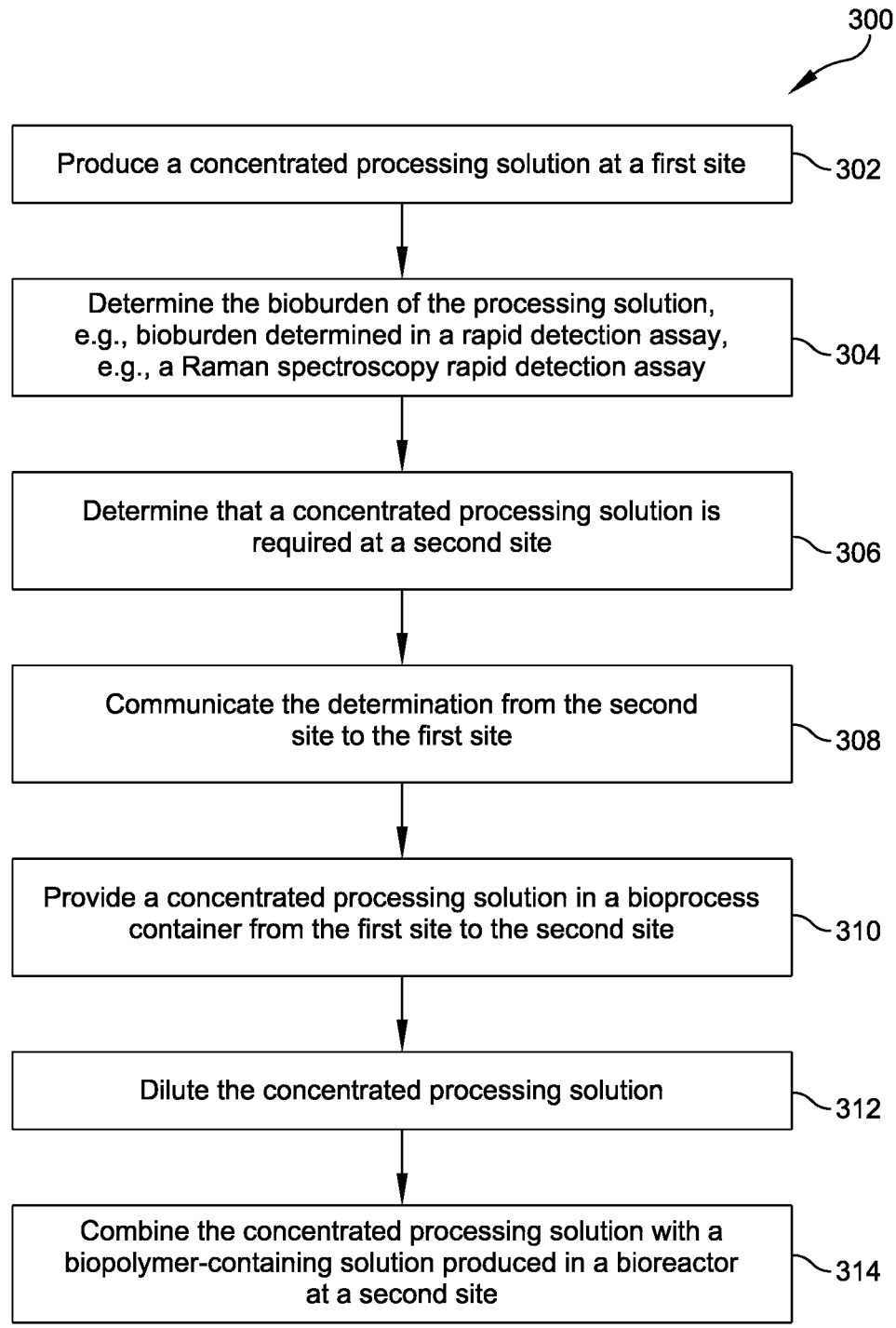
FIG. 3 is a block diagram of an embodiment of a method according to the present disclosure.

Referring now to FIG. 3, the present disclosure provides a method 300 for delivering a processing solution, the system. In FIG. 3, an exemplary embodiment of the method 300 for delivering a processing solution includes producing a concentrated processing solution at a first site at 302. In some embodiments, the processing solution is a buffer.

In some embodiments, the buffer is Tris, Tricine, HEPES, MOPS, PIPES, TAPS, bicine, BES, TES, cacodylate, MES, acetate, MKP, ADA, ACES, glycinamide and acetamidoglycine or acetic acid or a buffer as shown in Tables 6-9.

In some embodiments, at 304, the method 300 determines the bioburden of the processing solution. Step 304 can be performed entirely or in part by a controller, such as the controller 140 in FIG. 2. At step 304, the method 300 determines that the processing solution meets quality standards. This allows a user to reduce the risk that a product from the bioreactor (or other downstream processing unit) will be contaminated. Any bioburden testing method can be implemented. In some embodiments, the bioburden can be determined in a rapid detection assay. In some embodiments, the bioburden is determined in a Raman spectroscopy rapid detection assay. In some embodiments, the bioburden testing can be an in-line or at-line test performed at either the processing solution production site or a second site where the processing solution is to be used.

At 306, the method 300 determines that the concentrated processing solution is required at the second site. At 308, the method communicates this determination from the second site to the first site. This determination at step 306 can be performed by a controller connected to a bioreactor at the second site, such as the controller 140 shown in FIG. 2. The concentrated processing solution is then provided to the second site 108 based on the determination.

At 310, the method 300 provides a concentrated processing solution in a bioprocess container, the concentrated processing solution produced at a first site. In some embodiments, step 310 includes transporting one or more bioprocess containers containing the processing solution from the first site to the second site.

In some embodiments, the bioprocess container includes an inner layer for contacting the process solution and an outer layer. In some embodiments, the inner layer is polyethylene. In some embodiments, the outer layer is a blend of polyethylene, EVOH, nylon, and PVDC.

At 312, the method 300 includes diluting the concentrated processing solution prior to combining with the biopolymer containing solution. For example, in some embodiments, step 312 of the method 300 includes adding concentrated processing solution from a processing solution supply and water or buffer from the water/buffer supply to an inlet of an inline processing solution dilution system to result in a diluted processing solution.

At 314, the method 300 combines the concentrated processing solution with a biopolymer-containing solution produced in a bioreactor at the second site, which is different from the first site.

The compositions, systems, and methods of the disclosure provide extended stability data and allow for long term storage of process intermediates. This allows an operator to decouple production of a biologic product from production of an intermediate used to process the biologic product. A further advantage of the disclosure is that it allows for a concentrated buffer solution to be produced at a site remote from the site of biologic production. The concentrated buffers can be produced in a low value production facility and thus frees up space in a high value production facility occupied by the bioreactor. In addition to reducing manufacturing costs, the extended stability time allows for review and release of GMP paperwork. Process intermediates impacted by a GMP error or failed quality test etc. can be rejected, thus removing risk to the biologics production.

The combined use of concentrated buffer supplied in BPCs from a remote preparation area, in line dilution and long expiry times for the buffer solutions results in a cheaper and less risk laden buffer supply strategy.

Figure 4A:
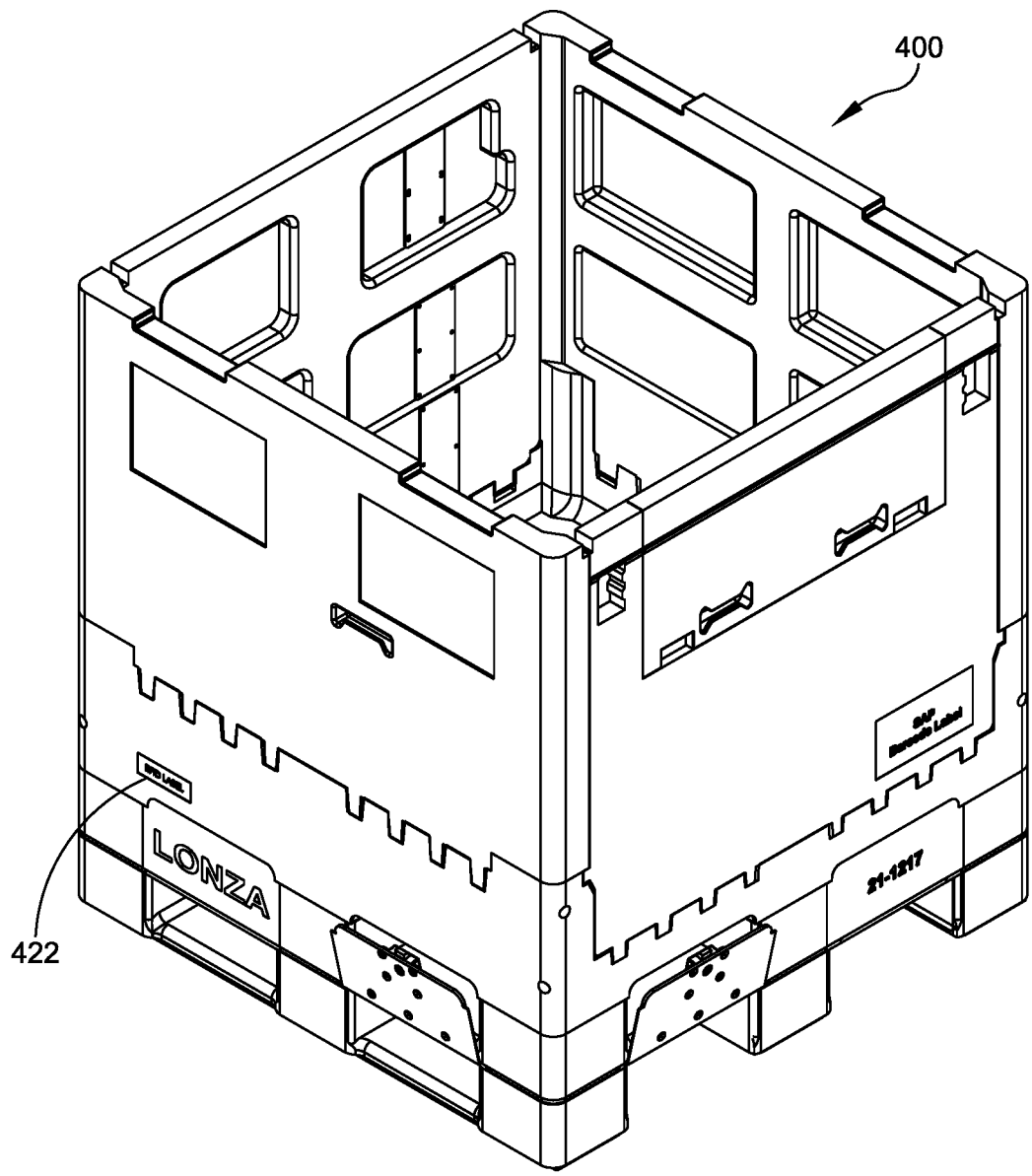
FIG. 4A shows a perspective view of an embodiment of an outer layer of a bioprocess container.

The systems and methods of the present disclosure can use various bioprocess containers. FIGS. 4A-4F show an outer layer generally indicated at 400 of an embodiment of a bioprocess container. The outer layer 400 can be used to support an inner layer, such as a bag, for containing a buffer within the inner layer. The lower end of the outer layer 400 of the bioprocess container includes a portion that can be lifted by a forklift. FIG. 4A shows a perspective view of the bioprocess container.

Figure 4B:
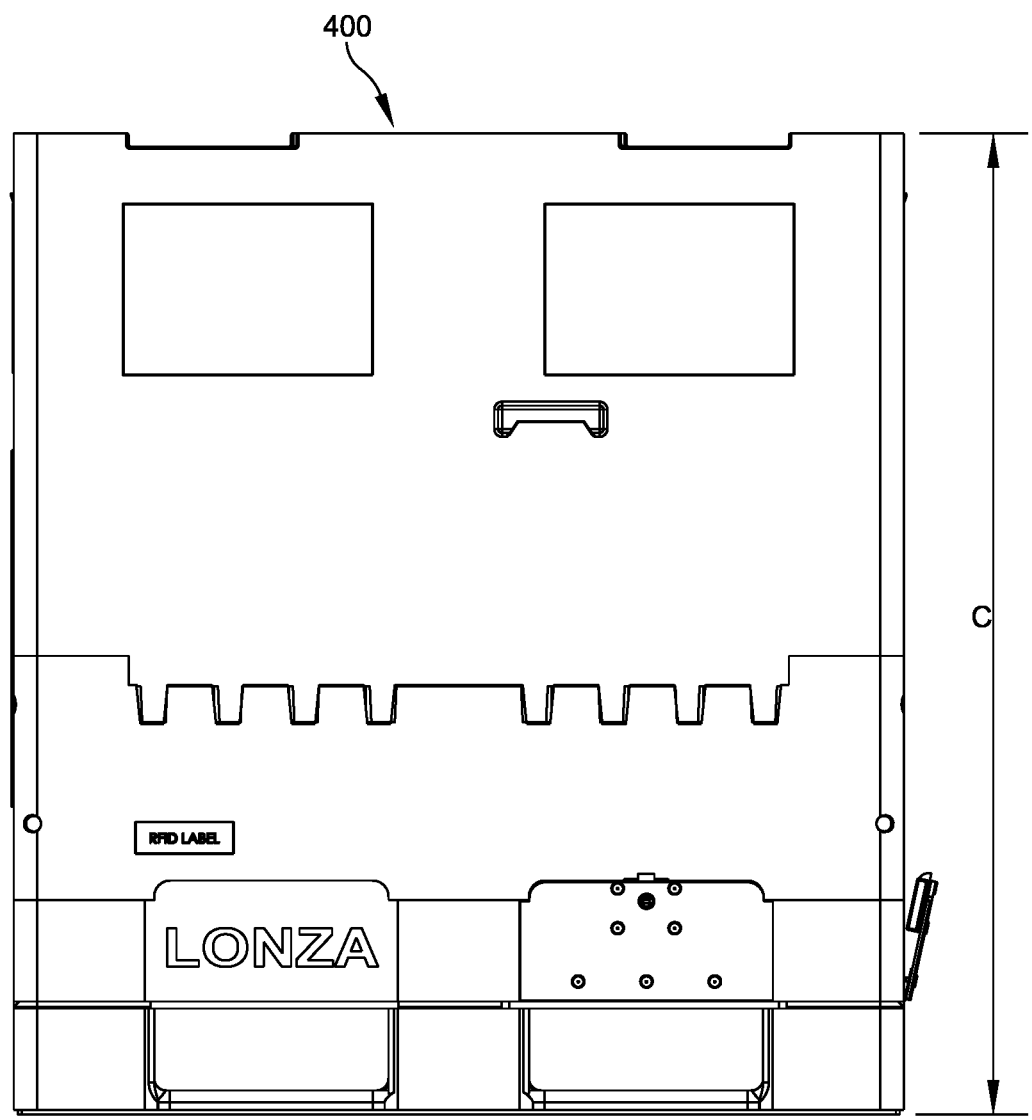
FIG. 4B shows a side view thereof.
Figure 4C:
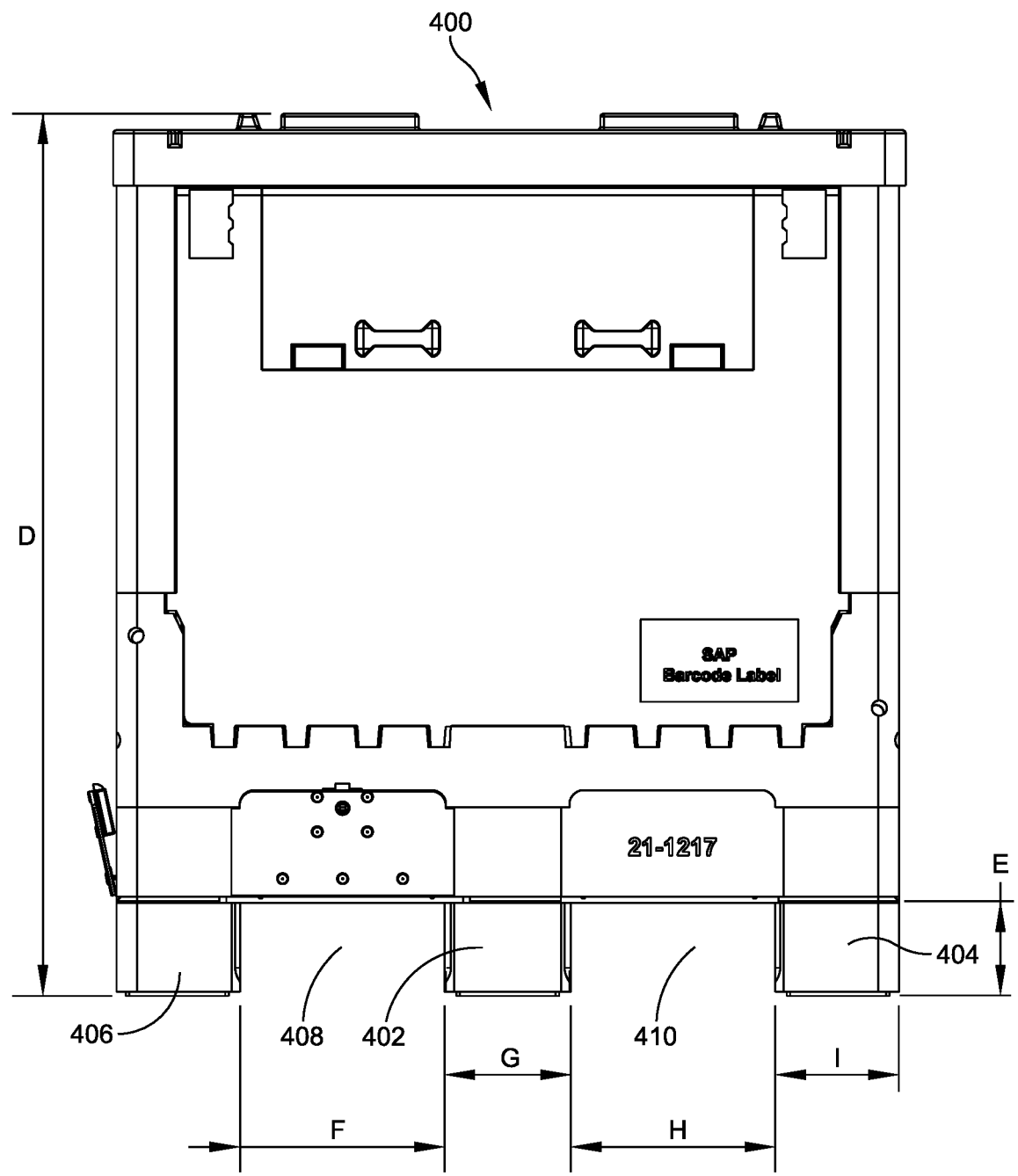
FIG. 4C shows a rear view thereof.
Figure 4D:
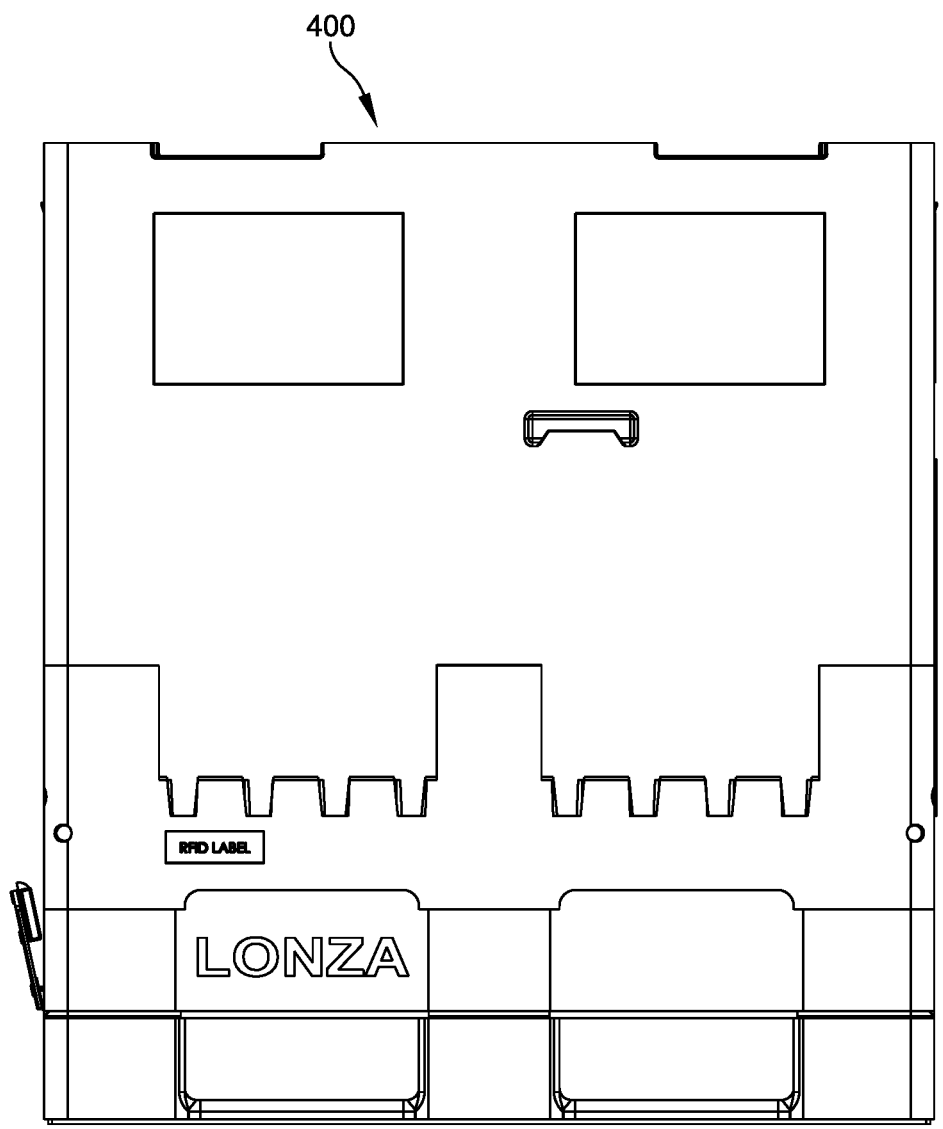
FIG. 4D shows a side view thereof.
Figure 4E:
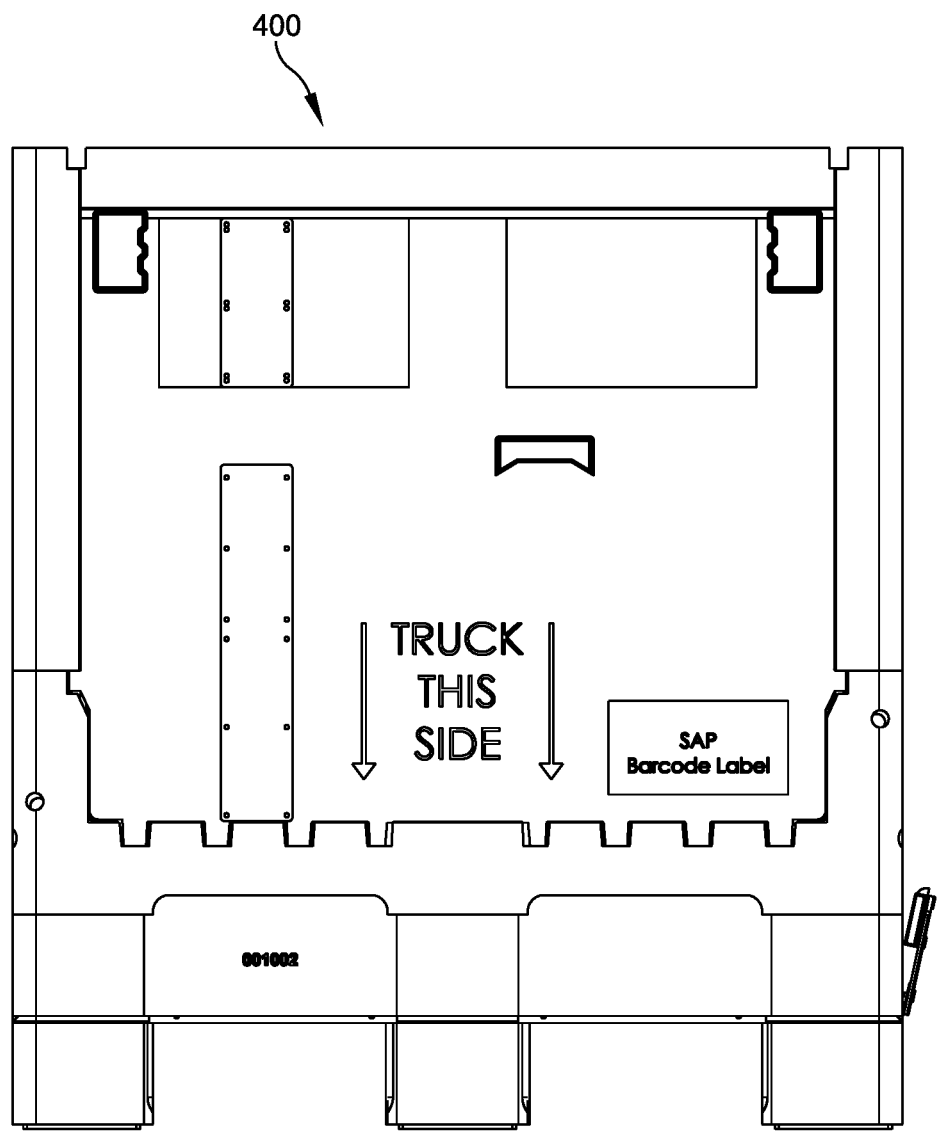
FIG. 4E shows a front view thereof.

In FIG. 4B, the bioprocess container has an overall height C of 1264 millimeters. FIG. 4C shows another side of the bioprocess container having a height D of 1287 millimeters when a lid is secured to the outer layer 400 of the bioprocess container.

The lower end of the bioprocess container can be engaged by a forklift and includes base portions 402, 404, 406 that define recesses 408, 410. Each of the recesses 408, 410 has a height E of 135 millimeters. A first recess 408 has a width F of 310 millimeters. A second recess 410 has a width H of 310 millimeters. A first base portion 402 has a width G of 160 millimeters. A second base portion 404 has a width I of 180 millimeters.

Figure 4F:
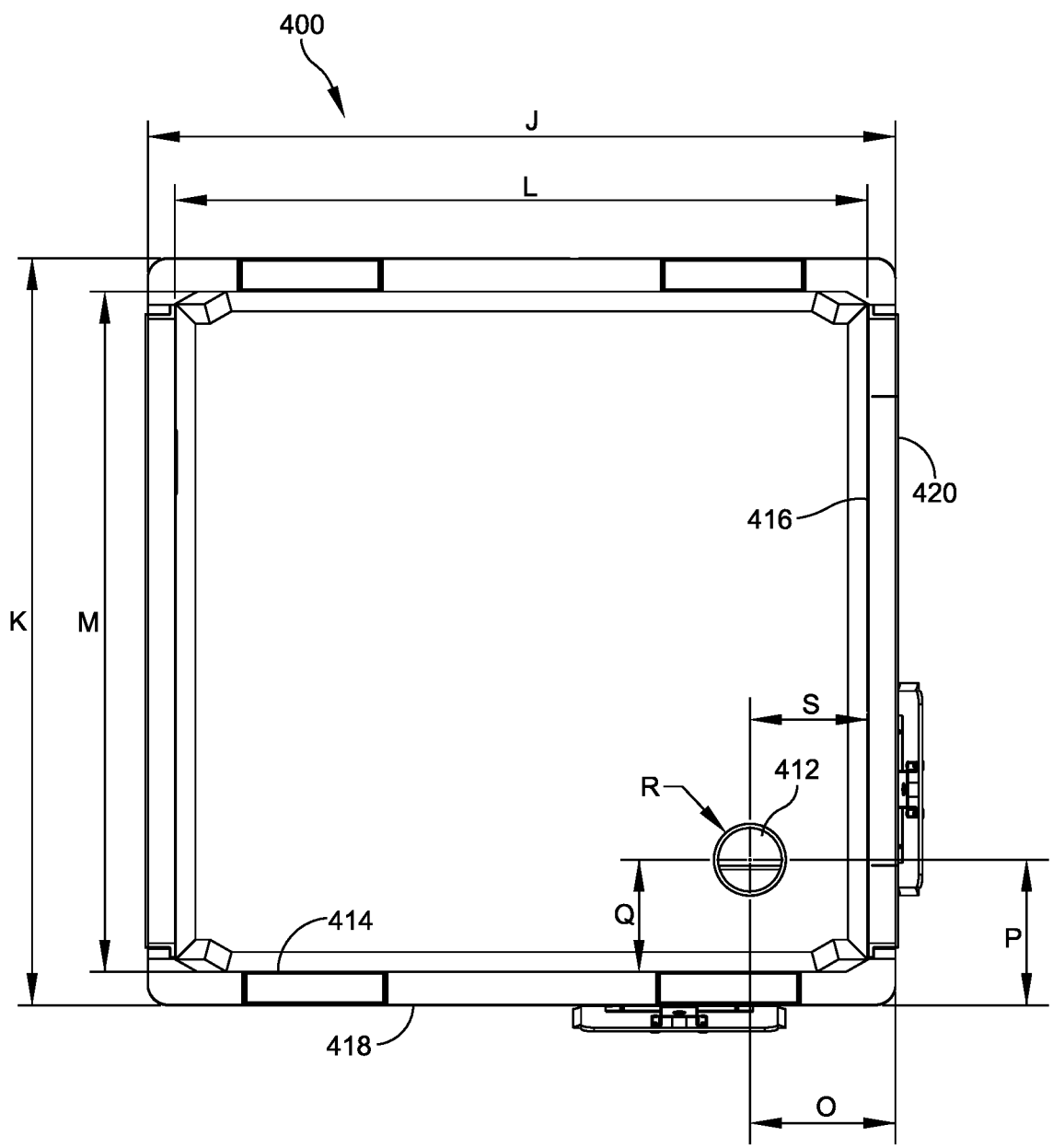
FIG. 4F shows a top view thereof.

In FIG. 4F, the top view of the outer layer 400 of the bioprocess container has a length J of 1140 millimeters and a width K of 1140 millimeters. The inner volume of the outer layer 400 of the bioprocess container is defined by inner length L and inner width M. The inner length L is 1056 millimeters and the inner width M is 1038 millimeters.

A port 412 is defined in the outer layer 400 of the bioprocess container for dispensing process solution from the bioprocess container. The port 412 has a diameter R of 97 millimeters. The port 412 is offset from a first inner surface 414 of the outer layer 400 of the bioprocess container by dimension Q, which is 171 millimeters. The port 412 is offset from a second inner surface 416 of the outer layer 400 of the bioprocess container by dimension S, which is 181 millimeters. The port 412 is offset from a first outer surface 418 by dimension P, which is 222 millimeters. The port 412 is offset from a second outer surface 420 of the by dimension O, which is 222 millimeters.

In some embodiments, the inner layer (bag) of the bioprocess container includes outlet tubing that is threaded through the port 412 of the outer layer 400.

Figure 5:
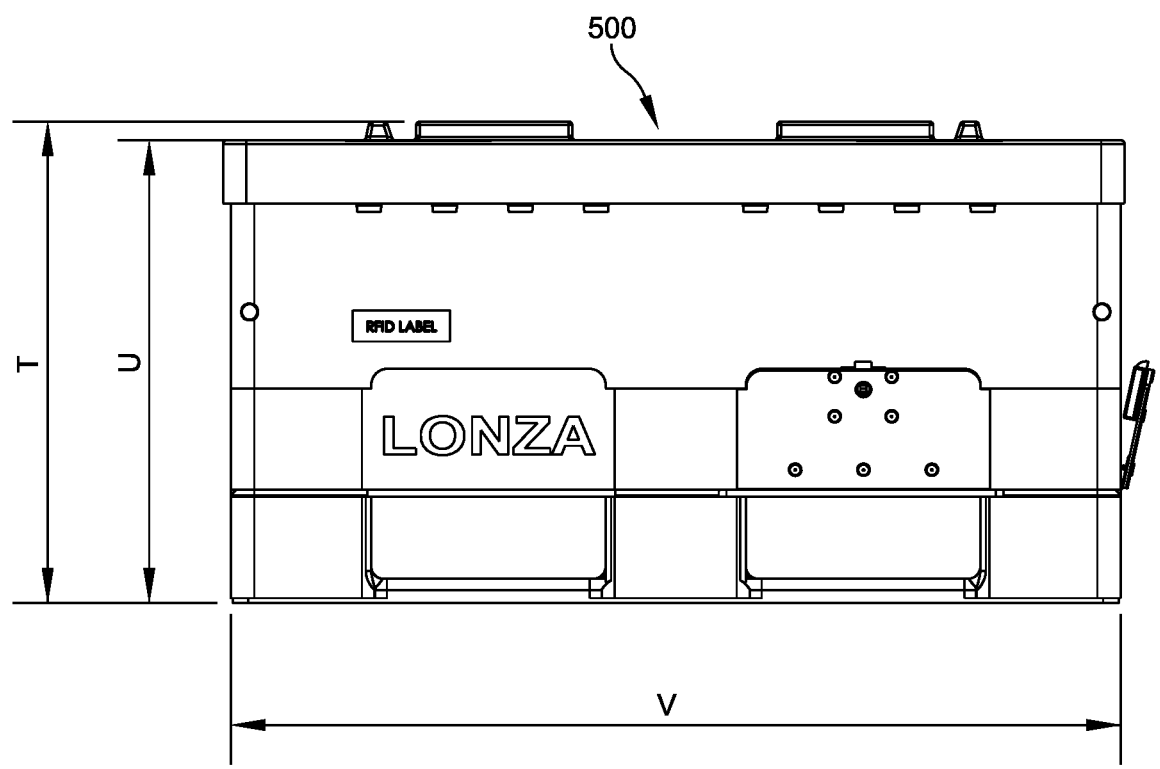
FIG. 5 shows a side view of another embodiment of an outer layer of a bioprocess container.

FIG. 5 shows another embodiment of an outer layer generally indicated at 500 of a bioprocess container. In FIG. 5, the outer layer 500 of the bioprocessing unit has a height U of 593 millimeters and a width V of 1140 millimeters. The height T of the outer layer 500 of the bioprocessing unit and the lid secured to the outer layer 500 is 617 millimeters.

In some embodiments, the bioprocess container includes a tracking system. For example, in some embodiments, the bioprocess container includes an RFID tag 422 (FIG. 4A) affixed to the outer layer 400 of the bioprocess container to facilitate tracking and management of the bioprocess container during shipping receiving. By including a respective RFID tag 422 on multiple bioprocess containers, a user can more easily manage inventory of bioprocess containers and more easily monitor the quality of the processing solution contained in the bioprocess container.

Figure 6A:
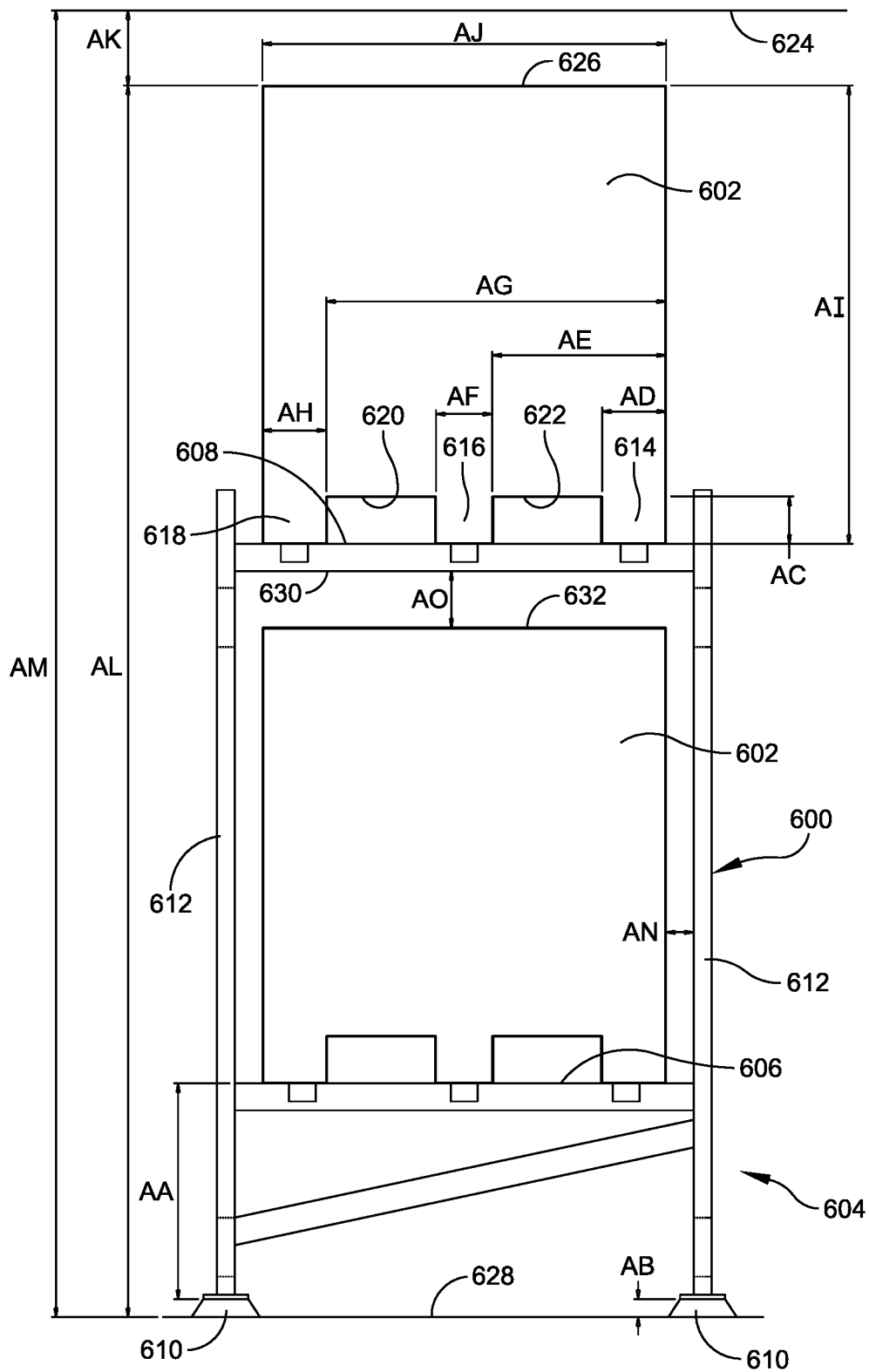
FIG. 6A shows a front view of an embodiment of a platform.

FIG. 6A shows a front view of an embodiment of a platform generally indicated at 600 for supporting bioprocess containers 602 to organize a buffer storage area 604. The platform 600 is configured to support at least one bioprocess container 602. This platform 600 can be used to support bioprocess containers in other embodiments of the buffer storage area, such as buffer storage area 126 of FIG. 2.

The platform 600 has a first level 606 configured to support at least one bioprocess container 602 and a second level 608 configured to support at least one bioprocess container 602. The platform 600 is configured to allow a user to place a bioprocess container 602 onto the platform 600 using a forklift, and the platform 600 is configured to allow a user to remove the respective bioprocess container 602 from the platform 600 using the forklift.

The first level 606 is offset from the ground by height AA, which is 2 feet. The platform is supported by feet, each indicated at 610, that have a height AB of 2 inches. Columns, each indicated at 612, extend upwardly from the feet 610, and support the first level 606 and the second level 608.

In FIG. 6A, a lower portion of a bioprocess container 602 includes three base portions 614, 616, 618 that define two recesses 620, 622. The recesses 620, 622 allow a user to operate a forklift to lift each bioprocess container 602 by accessing the respective bioprocess container 602 from the front of the platform 600.

The recesses 620, 622 have a height AC of 5 and 5/16 inches. The first base portion 614 has a width AD of 7 and 1/8 inches. The second base portion 616 is offset from a side of the bioprocess container 602 by a distance AE of one foot and 7 and 5/16 inches. The second base portion 616 has a width AF of 6 and 1/4 inches. The third base portion 618 is offset from a side of the bioprocess container 602 by a distance AG of 3 feet and 1 and 3/4 inches. The third base portion 618 has a width AH of 7 and 1/8 inches.

Each bioprocess container 602 has a height AI of 4 feet and 3 inches and a width AJ of 3 feet and 8 and 7/8 inches. The clearance AK between the bioprocess container 602 on the second level 608 of the platform 600 and the ceiling of the buffer storage area 604 is 6.5 inches. The overall height AL of the upper edge 626 of the bioprocess container 602 on the second level 608 of the platform 600 is 11 feet and five inches from the ground 628. The ceiling 624 is a height AM of 11 feet and 11.5 inches above the ground 628.

The bioprocess container 602 on the first level 606 is positioned between the columns 612 so there is a clearance AN of 3 inches between the bioprocess container 602 and at least one of the columns 612. There is a clearance AO of 6 and 3/8 inches between the lower surface 630 of the second level 608 and the upper surface 632 of the bioprocess container 602 that is positioned on the first level 606.

Figure 6B:
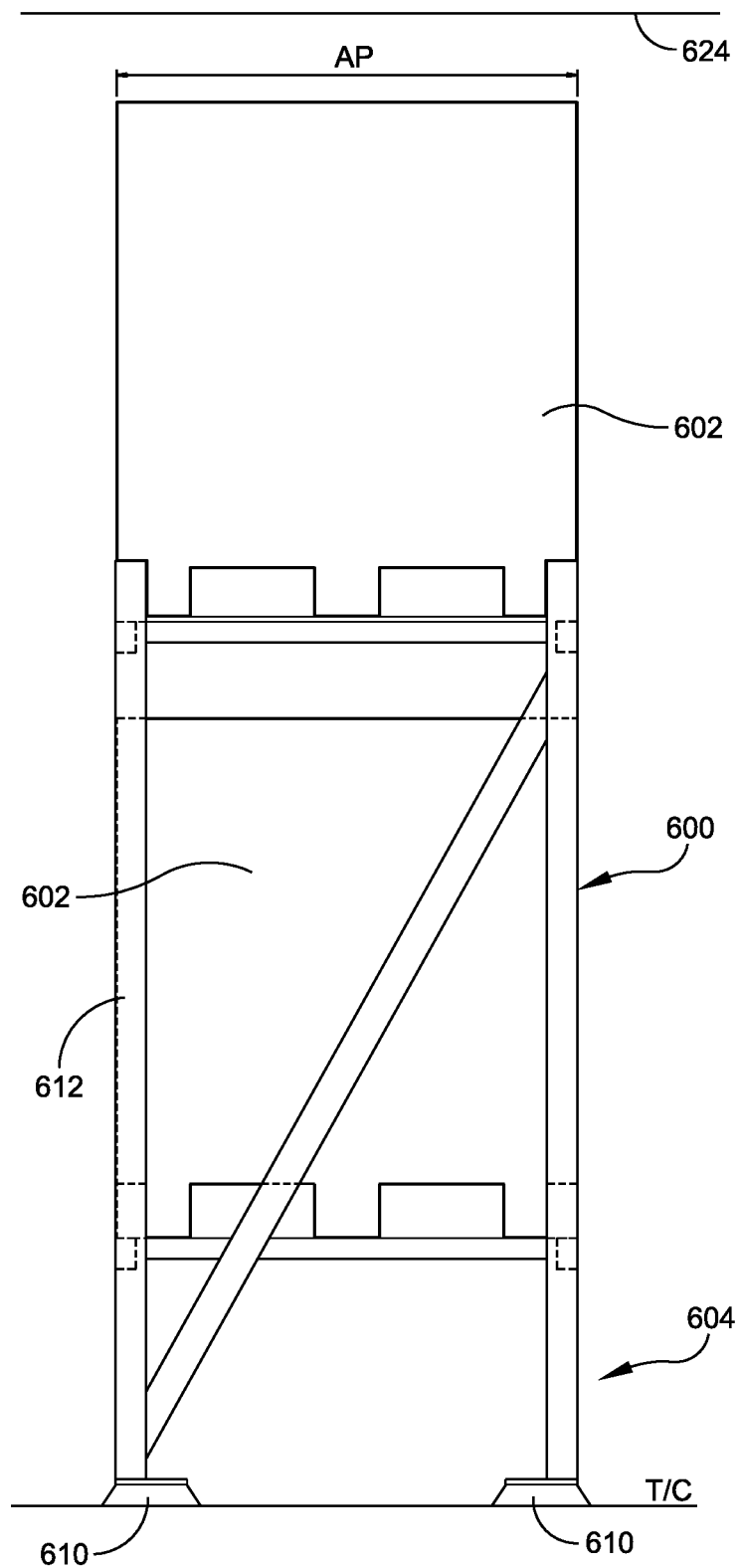
FIG. 6B shows a side view thereof.

FIG. 6B shows a side view of the platform 600 of FIG. 6A. FIG. 6B shows that the bioprocess container has a depth AP of 3 feet and 8 7/8 inches.

An aspect of the present disclosure relates to a pharmaceutical production facility having a buffer storage area capable of receiving at least one bioprocess container configured to contain a concentrated processing solution, a processing area capable of receiving at least one processing unit, and a wall separating the buffer storage area from the processing area. The facility also includes at least one pipe having a first end in the buffer storage area and a second end in the processing area. The first end is configured to connect to at least one bioprocess container, and the second end is configured to connect to at least one processing unit. In some embodiments, the processing area is configured as a cleanroom environment.

Figure 7A:
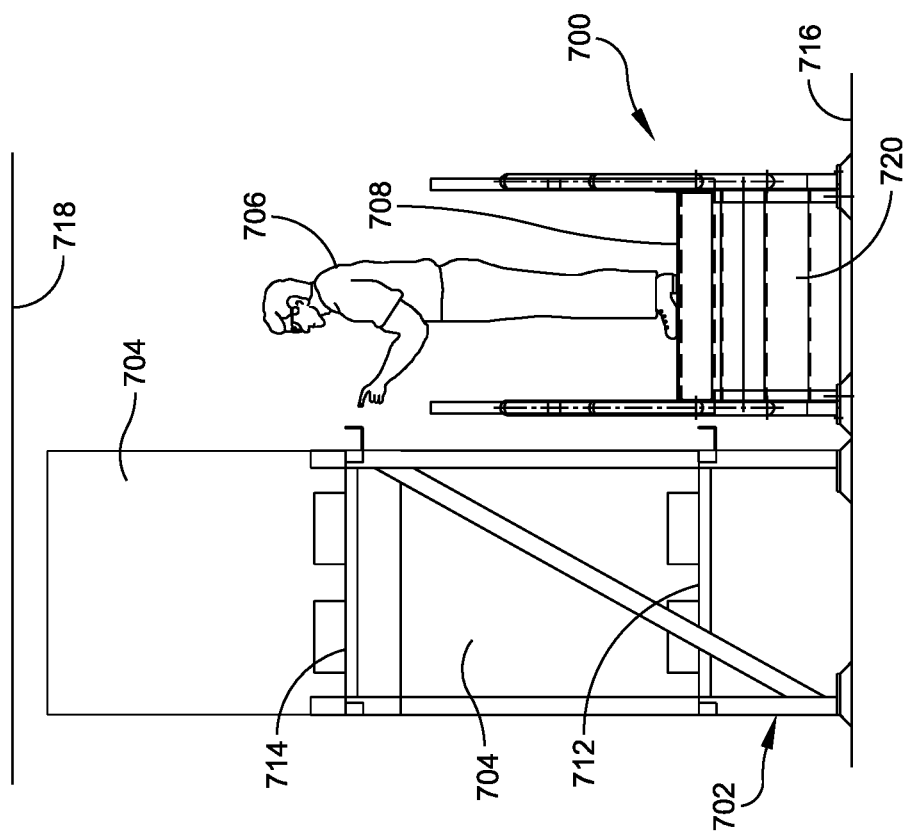
FIG. 7A shows a side view of an embodiment of a buffer storage area in a pharmaceutical production facility.

FIG. 7A shows a buffer storage area generally indicated at 700 that can be included in a pharmaceutical production facility. The buffer storage area 700 includes a platform 702 for supporting a plurality of bioprocess containers 704.

Each bioprocess container 704 includes an inner layer for contacting the processing solution and an outer layer configured to support the inner layer. Each bioprocess container 704 can be a bioprocess container of any of the embodiments shown and described herein.

FIG. 7A shows how a user 706 can access the bioprocess containers 704 from a user walkway 708 adjacent to the platform.

The pharmaceutical facility includes at least one pipe having a first end in the buffer storage area 700 and a second end in the processing area, such as a processing area as described in relation to various embodiments herein. The first end of each pipe is configured to connect to at least one bioprocess container 704, and the second end is configured to connect to at least one processing unit in the processing area. As described in relation to FIG. 2, each pipe can include a valve.

Figure 7C:
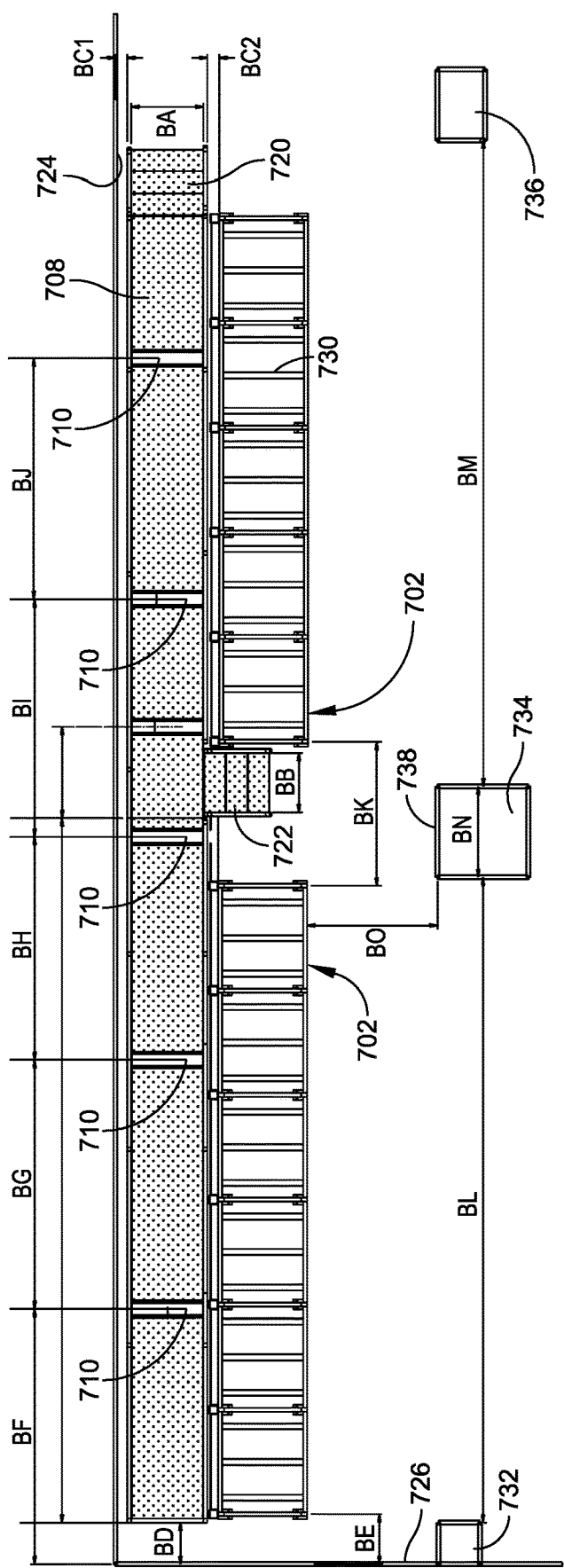
FIG. 7C shows a top view thereof.
Figure 7B:
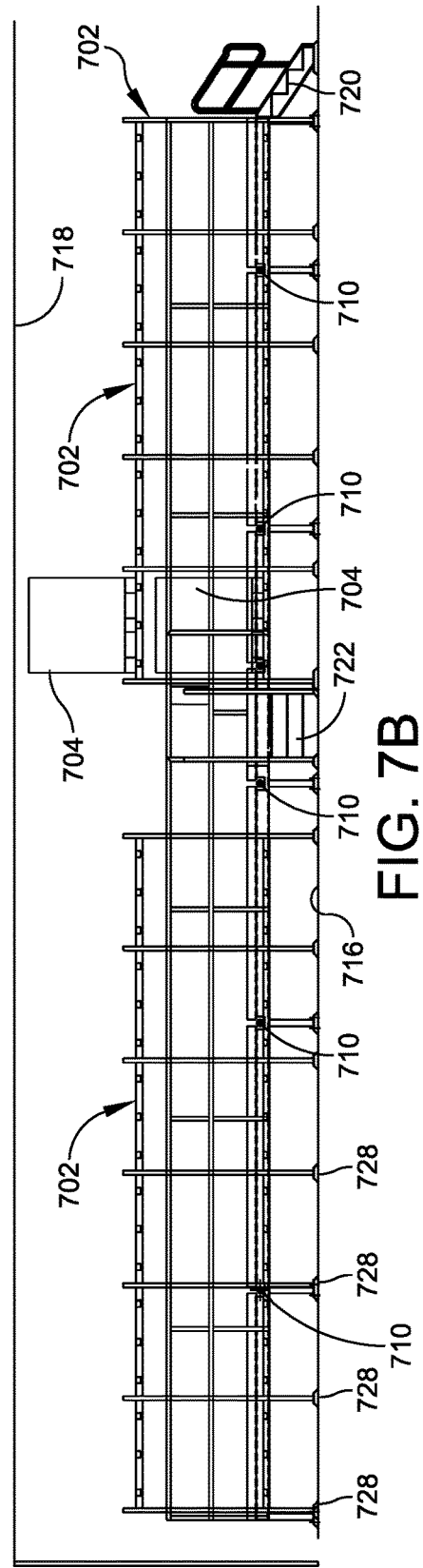
FIG. 7B shows a front view thereof.

FIG. 7B shows that the buffer storage area 700 includes a plurality of inlets, each indicated at 710 spaced apart along a length of the platform 702. Each inlet 710 is connected to the pipe(s). Each inlet 710 is configured to be connected to an outlet of a bioprocess container. The inlets 710 and the pipe(s) allow buffer to flow from one or more of the bioprocess container(s) 704 to a processing unit in the processing area.

Referring back additionally to FIG. 7A, the platform 702 supports bioprocess containers 704 on a first level 712 of the platform 702 and on a second level 714 of the platform between a floor 716 and a ceiling 718 of the buffer storage area 700. The platform 702 allows a user 706 to organize the bioprocess containers 704 in a way that efficiently uses the space of the buffer storage area 700 and that allows the user to place the bioprocess containers 704 on the platform 702 and remove the bioprocess containers 704 from the platform 702 using a forklift.

In embodiments in which the bioprocess containers 704 include a tracking system, such as a barcode or an RFID tag affixed to each bioprocess container 704, the user walkway 708 allows a user to easily access the bioprocessing units to take inventory of the bioprocess containers 704 or to collect information such as the age of the bioprocess containers 704.

The user walkway 708 also allows a user 706 to connect a port on one of the bioprocess containers 704 to an inlet 710 so that process solution from that bioprocess container 704 can flow from the bioprocess container 704 through the inlet 710 and the pipe to one or more processing unit(s) in the processing area.

The top view of FIG. 7C shows that the walkway 708 has a width BA of 3 feet.

The walkway 708 is connected to two stairways 720, 722. The walkway 708 and the first stairway 720 each has a width BA of 3 feet. The second stairway 722 has a width BB of 2.5 feet. The walkway 708 is positioned a distance BC1 of 6 inches from a rear wall 724 and a distance BC2 of 6 inches from each platform 702. The walkway 708 is positioned a distance BD of 1 foot and 9 inches from a side wall 726.

The platform 702 includes feet, each indicated at 728. The foot 728 closest to the side wall 726 is centered a distance BE of 2 feet and 1.25 inches from the side wall 726.

The inlets 710 are spaced apart, with a first inlet 710 being a distance BF of 10.75 feet from the side wall 726, a second inlet 710 being a distance BG of 10.5 feet from the first inlet 710, a third inlet being a distance BH of 9 feet five inches from the second inlet 710, a fourth inlet 710 being a distance BI of 10 feet from the third inlet 710, and a fifth inlet 710 being a distance BJ of 10 feet 2 inches from the fourth inlet 710.

Two platforms 702 are included in the buffer storage area 700. Each platform 702 includes frame members 730 having a cross section of 3 inches wide and 2 inches high. The platforms 702 are spaced apart by a distance BK of 6 feet and 5/8 inches Building support columns 732, 734, 736 extend between the floor 716 and the ceiling 718. The distance BL between the first support column 732 and the second support column 734 is 27 feet and 2.5 inches. The distance BM between the second support column 734 and the third support column 736 is 27 feet and 2.5 inches. The width BN of the second support column 734 is 3 feet and 10 inches. A face 738 of the second support column is a distance BO of 6 feet and 7 inches from the front edge of the platforms 702.

The dimensions discussed in relation to FIGS. 4A-7C are exemplary and can be changed to suit a particular facility.

Definitions

Unless defined otherwise, all technical and scientific terms used herein have the same meaning as commonly understood by one of ordinary skill in the art to which the disclosure pertains. Although any methods and materials similar or equivalent to those described herein can be used in the practice of and/or for the testing of the present disclosure, the preferred materials and methods are described herein. In describing and claiming the present disclosure, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "a cell" can mean one cell or more than one cell.

As used herein, "processing solution" means a buffer or media used in a biologic manufacturing process including solutions used in upstream and downstream processing.

As used herein a downstream processing agent (DPA) is a biocompatible solution that contains one or more ingredients that act upon a product of a bioreactor or associated component, e.g., a cell cultured in a bioreactor, for downstream processing operations performed on the target molecule. Examples of suitable DPAs include, e.g., buffered saline solution such as HBSS, PBS, TRIS, Acetic acid or similar A DPA as used herein is thus distinct from a medium, which does support growth and division of cells. The DPAs of the disclosure provide a physiologically equivalent physicochemical environment without supporting cell growth and/or division.

DPAs are commonly used in downstream processing for biologics manufacture and heretofore are produced in a GMP manner temporally close coupled to a production batch. In addition to adding time and cost, this results in in-process material being used prior to completion of long lead testing and/or review and release of GMP records (batch records) as such in process material is used "at risk". Using unreleased material risks the possibility that a GMP error could be uncovered after the use of the process intermediate that would introduce risk to product quality, these can include instrument calibration errors and the like. This method is used because buffers can have assigned use by dates of days and stockpiling buffers occupies a large amount of GMP processing space.

As used herein, the term "bioburden" refers to the level of self-replicating biological contaminants present in a composition (e.g., solid or liquid) and/or on the surface (e.g., exterior and/or interior surface) of an article(s). For example, bioburden can refer to self-replicating biological contaminants present in a composition containing a chromat the term "bioburden" is art known and refers to the level of self-replicating biological contaminants present in a composition (e.g., solid or liquid) and/or on the surface (e.g., exterior and/or interior surface) of an article(s). In other examples, bioburden can to refer to self-replicating biological contaminants on the inner surface of a chromatography column and/or within the chromatography resin within the chromatography column (e.g., biological contaminants on the inner surface of a chromatography column and biological contaminants in the packed chromatography resin within the chromatography column). Bioburden can also refer to the self-replicating biological contaminants present within a liquid (e.g., a buffer used in any of the methods or processes described herein). Non-limiting examples of self-replicating biological contaminants can be bacteria (e.g., Gram-positive or Gram-negative bacteria, or a bacterial spore), mycobacteria, viruses (e.g., a vesivirus, a Cache Valley virus, a parvovirus, a herpes virus, and a bunyavirus), parasites, fungi, yeast, and protozoa.

As used herein, the term "endogenous" refers to any material from or naturally produced inside an organism, cell, tissue or system.

As used herein, the term "exogenous" refers to any material introduced to or produced outside of an organism, cell, tissue or system. Accordingly, "exogenous nucleic acid" refers to a nucleic acid that is introduced to or produced outside of an organism, cell, tissue or system. In an embodiment, sequences of the exogenous nucleic acid are not naturally produced, or cannot be naturally found, inside the organism, cell, tissue, or system that the exogenous nucleic acid is introduced into. In one embodiment, the sequences of the exogenous nucleic acids are non-naturally occurring sequences, or encode non-naturally occurring products.

As used herein, the term "heterologous" refers to any material from one species, when introduced to an organism, cell, tissue or system from a different species.

As used herein, the terms "nucleic acid," "polynucleotide," or "nucleic acid molecule" are used interchangeably and refers to deoxyribonucleic acid (DNA) or ribonucleic acid (RNA), or a combination of a DNA or RNA thereof, and polymers thereof in either single- or double-stranded form. The term "nucleic acid" includes, but is not limited to, a gene, cDNA, or an mRNA. In one embodiment, the nucleic acid molecule is synthetic (e.g., chemically synthesized or artificial) or recombinant. Unless specifically limited, the term encompasses molecules containing analogues or derivatives of natural nucleotides that have similar binding properties as the reference nucleic acid and are metabolized in a manner similar to naturally or non-naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

As used herein, the terms "peptide," "polypeptide," and "protein" are used to refer to a compound comprised of amino acid residues covalently linked by peptide bonds, or by means other than peptide bonds. A protein or peptide must contain at least two amino acids, and no limitation is placed on the maximum number of amino acids that can comprise a protein's or peptide's sequence. In one embodiment, a protein may comprise of more than one, e.g., two, three, four, five, or more, polypeptides, in which each polypeptide is associated to another by either covalent or non-covalent bonds/interactions. Polypeptides include any peptide or protein comprising two or more amino acids joined to each other by peptide bonds or by means other than peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others.

As used herein, "product" refers to a molecule, e.g., a protein, nucleic acid, polypeptide, or any hybrid thereof, that is produced, e.g., expressed, by a cell which has been modified or engineered to produce the product. In one embodiment, the product is a naturally occurring product or a non-naturally occurring product, e.g., a synthetic product. In one embodiment, a portion of the product is naturally occurring, while another portion of the product is non-naturally occurring. In one embodiment, the product is a polypeptide, e.g., a recombinant polypeptide. In one embodiment, the product is suitable for diagnostic or pre-clinical use. In another embodiment, the product is suitable for therapeutic use, e.g., for treatment of a disease. In one embodiment, the product is selected from Table 1 or Table 2. In one embodiment, the modified or engineered cells comprise an exogenous nucleic acid that controls expression or encodes the product. In other embodiments, the modified or engineered cells comprise other molecules, e.g., that are not nucleic acids, that controls the expression or construction of the product in the cell.

In one embodiment, the modification of the cell comprises the introduction of an exogenous nucleic acid comprising a nucleic acid sequence that controls or alters, e.g., increases, the expression of an endogenous nucleic acid sequence, e.g., endogenous gene. In such embodiments, the modified cell produces an endogenous polypeptide product that is naturally or endogenously expressed by the cell, but the modification increases the production of the product and/or the quality of the product as compared to an unmodified cell, e.g., as compared to endogenous production or quality of the polypeptide.

In another embodiment, the modification of the cell comprises the introduction of an exogenous nucleic acid encoding a recombinant polypeptide as described herein. In such embodiments, the modified cell produces a recombinant polypeptide product that can be naturally occurring or non-naturally occurring. In such embodiments, the modified cell produces a recombinant polypeptide product that can also be endogenously expressed by the cell or not. In embodiments where the recombinant polypeptide product is also endogenously expressed by the cell, the modification increases the production of the product and/or the quality of the product as compared to an unmodified cell, e.g., as compared to endogenous production or quality of the polypeptide.

As used herein, "recombinant polypeptide" or "recombinant protein" refers to a polypeptide that can be produced by a cell described herein. A recombinant polypeptide is one for which at least one nucleotide of the sequence encoding the polypeptide, or at least one nucleotide of a sequence which controls the expression of the polypeptide, was formed by genetic engineering (of the cell or of a precursor cell). E.g., at least one nucleotide was altered, e.g., it was introduced into the cell or it is the product of a genetically engineered rearrangement. In an embodiment, the sequence of a recombinant polypeptide does not differ from a naturally occurring isoform of the polypeptide or protein. In an embodiment, the amino acid sequence of the recombinant polypeptide differs from the sequence of a naturally occurring isoform of the polypeptide or protein. In an embodiment, the recombinant polypeptide and the cell are from the same species. In an embodiment, the recombinant polypeptide is endogenous to the cell, in other words, the cell is from a first species and the recombinant polypeptide is native to that first species. In an embodiment, the amino acid sequence of the recombinant polypeptide is the same as or is substantially the same as, or differs by no more than 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% from, a polypeptide encoded by the endogenous genome of the cell. In an embodiment, the recombinant polypeptide and the cell are from different species, e.g., the recombinant polypeptide is a human polypeptide and the cell is a non-human, e.g., a rodent, e.g., a CHO, or an insect cell. In an embodiment, the recombinant polypeptide is exogenous to the cell, in other words, the cell is from a first species and the recombinant polypeptide is from a second species. In one embodiment, the polypeptide is a synthetic polypeptide. In one embodiment, the polypeptide is derived from a non-naturally occurring source. In an embodiment, the recombinant polypeptide is a human polypeptide or protein which does not differ in amino acid sequence from a naturally occurring isoform of the human polypeptide or protein. In an embodiment, the recombinant polypeptide differs from a naturally occurring isoform of the human polypeptide or protein at no more than 1, 2, 3, 4, 5, 10, 15 or 20 amino acid residues. In an embodiment, the recombinant polypeptide differs from a naturally occurring isoform of the human polypeptide by no more than 1, 2, 3, 4, 5, 6, 7, 8, 9, 10, or 15% of its amino acid residues.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

Chromatography and Spectroscopy Techniques

The processing solutions can be used along with chromatographic and/or spectroscopic methods to further purify, or assess the purity of solutions. Methods of 1-dimensional (1D) chromatography suitable for use in the methods described here are known to one of skill in the art and include, e.g., affinity chromatography, gel filtration chromatography, ion exchange chromatography, reversed phase chromatography, hydrophobic interaction chromatography. In some embodiments, the one-dimensional chromatography method is HPLC reversed phase chromatography. Chromatography can include high performance liquid chromatography (HPLC), gas chromatography (GC), capillary electrophoresis, ion mobility. See also, e.g., Process Scale Purification of Antibodies, Uwe Gottschalk 2011 John Wiley & Sons ISBN: 1118210743; Antibodies Vol 1 Production and Purification, G. Subramanian 2013 Springer Science & Business Media; Basic Methods in Antibody Production and Characterization, Gary C. Howard 2000 CRC Press.

Additional exemplary chromatographic methods include, but are not limited to, Strong Anion Exchange chromatography (SAX), liquid chromatography (LC), high performance liquid chromatography (HPLC), ultra performance liquid chromatography (UPLC), thin layer chromatography (TLC), amide column chromatography, and combinations thereof. Exemplary mass spectrometry (MS) include, but are not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof. Exemplary electrophoretic methods include, but are not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof. Exemplary nuclear magnetic resonance (NMR) include, but are not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

Suitable spectroscopic techniques include, e.g., Raman spectroscopy. Raman spectroscopy is a technique that is increasing in popularity among the different disciplines of forensic science. Some examples of its use today involve the identification of drugs (Hodges et al., "The Use of Fourier Transform Raman Spectroscopy in the Forensic Identification of Illicit Drugs and Explosives," Molecular Spectroscopy 46:303-307 (1990)), lipsticks (Rodger et al., "The In-Situ Analysis of Lipsticks by Surface Enhanced Resonance Raman Scattering," Analyst 1823-1826 (1998)), and fibers (Thomas et al., "Raman Spectroscopy and the Forensic Analysis of Black/Grey and Blue Cotton Fibres Part 1: Investigation of the Effects of Varying Laser Wavelength," Forensic Sci. Int. 152:189-197 (2005)), as well as paint (Suzuki et al., "In Situ Identification and Analysis of Automotive Paint Pigments Using Line Segment Excitation Raman Spectroscopy: I. Inorganic Topcoat Pigments," J. Forensic Sci. 46:1053-1069 (2001)) and ink (Mazzella et al., "Raman Spectroscopy of Blue Gel Pen Inks," Forensic Sci. Int. 152:241-247 (2005)) analysis. The theory behind Raman spectroscopy is based on the inelastic scattering of low-intensity, nondestructive laser light by a solid, liquid or gas sample. Very little or no sample preparation is needed, and the required amount of tested material could be as low as several picograms or femtoliters ($10^{-12}$ gram or $10^{-15}$ liter, respectively). A typical Raman spectrum consists of several narrow bands and provides a unique vibrational signature of the material (Grasselli et al., "Chemical Applications of Raman Spectroscopy," New York: John Wiley & Sons (1981)). Unlike infrared (IR) absorption spectroscopy, another type of vibrational spectroscopy, Raman spectroscopy shows very little interference from water (Grasselli et al., "Chemical Applications of Raman Spectroscopy," New York: John Wiley & Sons (1981)), and that makes it a great technique for analyzing body fluids and their traces. Proper Raman spectroscopic measurements do not damage the sample. The stain or swab could be tested on the field and still be available for further use in the lab for DNA analysis, and that is very important to forensic application. The design of a portable Raman spectrometer is a reality now (Yan et al., "Surface-Enhanced Raman Scattering Detection of Chemical and Biological Agents Using a Portable Raman Integrated Tunable Sensor," Sensors and Actuators B. 6 (2007); Eckenrode et al., "Portable Raman Spectroscopy Systems for Field Analysis," Forensic Science Communications 3:(2001)) which would lead to the ability to make identifications at the crime scene.

The types of Raman spectroscopy suitable for use in conjunction with the present disclosure include, but are not limited to conventional Raman spectroscopy, Raman microspectroscopy, near-field Raman spectroscopy, including but not limited to the tip-enhanced Raman spectroscopy, surface enhanced Raman spectroscopy (SERS) and surface enhanced resonance Raman spectroscopy (SERRS), coherent anti-Stokes Raman spectroscopy (CARS), etc. Both Stokes and anti-Stokes Raman spectroscopy can be used.

In some embodiments, a rapid non-invasive test is performed on one or more bioprocessing intermediates using the chromatographic or spectroscopic methods described herein. In some embodiments, the rapid test is performed using Ramon spectroscopy.

Mass Spectrometry

Mass spectrometry methods suitable for use in the methods described herein are known to one of skill in the art and include, e.g., electrospray ionization MS, matrix-assisted laser desportion/ionization MS, time of flight MS, fourier-transform ion cyclotron resonance MS, quadrupole time of flight MS, linear quadrupole, quadrupole ion trap MS, orbitrap, cylindrical ion trap, three dimensional ion trap, quadrupole mass filter, tandem mass spectrometry. In some embodiments, the mass spectrometry is tandem mass spectrometry. See also, e.g., Protein Mass Spectrometry, Julian Whitelegge 2008, Elsevier; Protein Sequencing and Identification Using Tandem Mass Spectrometry, Michael Kinter 2005, John Wiley & Sons; Characterization of Protein Therapeutics using Mass Spectrometry, Guodong Chen 2014, Springer Science & Business Media.

Production Parameters

Methods described herein include determining and/or selecting a production parameter or parameters for a glycoprotein preparation such that a preselected glycan property or properties can be obtained upon production of a glycoprotein preparation. By using information regarding the effects of various production parameters on glycosylation, production parameters can be selected prior to the production of a glycoprotein preparation that positively correlate with the desired glycan properties. A production parameter as used herein is a parameter or element in a production process. Production parameters that can be selected include, e.g., the cell or cell line used to produce the glycoprotein preparation, the culture medium, culture process or bioreactor variables (e.g., batch, fed-batch, or perfusion), purification process and formulation of a glycoprotein preparation.

Primary production parameters include: 1) the types of host; 2) genetics of the host; 3) media type; 4) fermentation platform; 5) purification steps; and 6) formulation. Secondary production parameter, as used herein, is a production parameter that is adjustable or variable within each of the primary production parameters. Examples include: selection of host subclones based on desired glycan properties; regulation of host gene levels constitutive or inducible; introduction of novel genes or promoter elements; media additives (e.g. partial list on Table IV); physiochemical growth properties; growth vessel type (e.g. bioreactor type, T flask); cell density; cell cycle; enrichment of product with a desired glycan type (e.g. by lectin or antibody-mediated enrichment, ion-exchange chromatography, CE, or similar method); or similar secondary production parameters clear to someone skilled in the art.

Media and Buffers

The methods described herein can include determining and/or selecting a media component and/or the concentration of a media component that has a positive correlation to a desired glycan property or properties. A media component can be added in or administered over the course of glycoprotein production or when there is a change media, depending on culture conditions. Media components include components added directly to culture as well as components that are a byproduct of cell culture.

Media components include, e.g., buffer, amino acid content, vitamin content, salt content, mineral content, serum content, carbon source content, lipid content, nucleic acid content, hormone content, trace element content, ammonia content, co-factor content, indicator content, small molecule content, hydrolysate content and enzyme modulator content.

Table 1 below provides examples of various media components that can be selected.

TABLE 1

Exemplary media components.

| | |
|---|---|
| Amino acids | Sugar precursors |
| Vitamins | Indicators |
| Carbon source (natural and unnatural) | Nucleosides or nucleotides |
| Salts | Butyrate or organics |
| Sugars | DMSO |
| Sera | Animal derived products |
| Plant derived hydrolysates | Gene inducers |
| Sodium pyruvate | Non-natural sugars |
| Surfactants | Regulators of intracellular pH |
| Ammonia | Betaine or osmoprotectant |
| Lipids | Trace elements |
| Hormones or growth factors | Minerals |
| Buffers | Non-natural amino acids |
| Non-natural amino acids | Non-natural vitamins |

Exemplary buffers include Tris, Tricine, HEPES, MOPS, PIPES, TAPS, bicine, BES, TES, cacodylate, MES, acetate, MKP, ADA, ACES, glycinamide and acetamidoglycine.

Minerals that are optionally present include bismuth, boron, calcium, chlorine, chromium, cobalt, copper, fluorine, iodine, iron, magnesium, manganese, molybdenum, nickel, phosphorus, potassium, rubidium, selenium, silicon, sodium, strontium, sulfur, tellurium, titanium, tungsten, vanadium, and zinc. Exemplary salts and minerals include CaCl2 (anhydrous), CuSO4 5H2O, Fe(NO3)·9H2O, KCl, KNO3, KH2PO4, MgSO4 (anhydrous), NaCl, NaH2PO4H2O, NaHCO3, Na2SE3 (anhydrous), ZnSO4·7H2O; linoleic acid, lipoic acid, D-glucose, hypoxanthine 2Na, phenol red, putrescine 2HCl, sodium pyruvate, thymidine, pyruvic acid, sodium succinate, succinic acid, succinic acid.Na.hexahydrate, glutathione (reduced), para-aminobenzoic acid (PABA), methyl linoleate, bacto peptone G, adenosine, cytidine, guanosine, 2'-deoxyadenosine HCl, 2'-deoxycytidine HCl, 2'-deoxyguanosine and uridine. When the desired glycan characteristic is decreased fucosylation, the production parameters can include culturing a cell, e.g., CHO cell, e.g., dhfr deficient CHO cell, in the presence of manganese, e.g., manganese present at a concentration of about 0.1 µM to 50 µM. Decreased fucosylation can also be obtained, e.g., by culturing a cell (e.g., a CHO cell, e.g., a dhfr deficient CHO cell) at an osmolality of about 350 to 500 mOsm. Osmolality can be adjusted by adding salt to the media or having salt be produced as a byproduct as evaporation occurs during production.

Production parameters can also include physiochemical parameters. Such conditions can include temperature, pH, osmolality, shear force or agitation rate, oxidation, spurge rate, growth vessel, tangential flow, DO, $CO_2$, nitrogen, fed batch, redox, cell density and feed strategy. Examples of physiochemical parameters that can be selected are provided in Table 2 below.

TABLE 2

Exemplary physiochemical parameters.

| | |
|---|---|
| pH | $CO_2$ |
| Osmolality | Nitrogen |
| shear force, or agitation rate | Fed batch |
| Oxidation | Redox |
| Spurge rate | Cell density |
| Growth vessel | Perfusion culture |
| Tangential flow | Feed strategy |
| Batch | Temperature |
| Dissolved O2 | Time of culture |

The system can be chosen based, at least in part, upon its correlation with a desired glycan property or properties. Cells can be grown, for example, as batch, fed-batch, perfusion, or continuous cultures. Production parameters that can be selected include, e.g., addition or removal of media including when (early, middle or late during culture time) and how often media is harvested; increasing or decreasing speed at which cell cultures are agitated; increasing or decreasing temperature at which cells are cultured; adding or removing media such that culture density is adjusted; selecting a time at which cell cultures are started or stopped; and selecting a time at which cell culture parameters are changed. Such parameters can be selected for any of the batch, fed-batch, perfusion and continuous culture conditions. A wide array of flasks, bottles, reactors, and controllers allow the production and scale up of cell culture systems.

Additional production parameters are known to one of skill in the art, see e.g., Antibody Expression and Production (2011) Ed. Mohamed Al-Rubeai; Springer Publishing.

Products and Nucleic Acids Encoding Them

Provided herein are methods for identifying, selecting, or making a cell or cell line capable of producing a product. The products encompassed by the present disclosure include, but are not limited to, molecules, nucleic acids, polypeptides (e.g., recombinant polypeptides, e.g., antibodies, bispecific antibodies, multispecific antibodies), or hybrids thereof, that can be produced by, e.g., expressed in, a cell. In some embodiments, the cells are engineered or modified to produce the product. Such modifications include the introducing molecules that control or result in production of the product. For example, a cell is modified by introducing an exogenous nucleic acid that encodes a polypeptide, e.g., a recombinant polypeptide, and the cell is cultured under conditions suitable for production, e.g., expression and secretion, of the polypeptide, e.g., recombinant polypeptide.

In embodiments, the cell or cell line identified, selected, or generated by the methods described herein produces a product, e.g., a recombinant polypeptide, useful in the treatment of a medical condition, disorder or disease.

Examples of medical conditions, disorders or diseases include, but are not limited to, metabolic disease or disorders (e.g., metabolic enzyme deficiencies), endocrine disorders (e.g., hormone deficiencies), haemostasis, thrombosis, hematopoietic disorders, pulmonary disorders, gastro-intestinal disorders, immunoregulation (e.g., immunodeficiency), infertility, transplantation, cancer, and infectious diseases.

In some embodiments, the product is an exogenous protein, e.g., a protein that is not naturally expressed by the cell. The product can be a therapeutic protein or a diagnostic protein, e.g., useful for drug screening. The therapeutic or diagnostic protein can be an antibody molecule, e.g., an antibody or an antibody fragment, a fusion protein, a hormone, a cytokine, a growth factor, an enzyme, a glycoprotein, a lipoprotein, a reporter protein, a therapeutic peptide, or a structural and/or functional fragment or hybrid of any of these.

In one embodiment, the product, e.g., recombinant polypeptide, is an antibody molecule. Products encompassed herein comprise diagnostic and therapeutic antibody molecules. A diagnostic antibody molecule includes an antibody, e.g., a monoclonal antibody or antibody fragment thereof, useful for imaging techniques. A therapeutic antibody molecule is suitable for administration to subjects, e.g., for treatment or prevention of a disease or disorder.

An antibody molecule is a protein, or polypeptide sequence derived from an immunoglobulin molecule which specifically binds with an antigen. In an embodiment, the antibody molecule is a full-length antibody or an antibody fragment. Antibodies and multiformat proteins can be polyclonal or monoclonal, multiple or single chain, or intact immunoglobulins, and may be derived from natural sources or from recombinant sources. Antibodies can be tetramers of immunoglobulin molecules. In an embodiment, the antibody is a monoclonal antibody. The antibody may be a human or humanized antibody. In one embodiment, the antibody is an IgA, IgG, IgD, or IgE antibody. In one embodiment, the antibody is an IgG1, IgG2, IgG3, or IgG4 antibody.

"Antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either VL or VH), camelid VHH domains, and multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3) (see U.S. Pat. No. 6,703,199, which describes fibronectin polypeptide minibodies).

Exemplary products, e.g., polypeptides, e.g., recombinant polypeptides, produced in the methods or cells described herein are provided in Tables 3 and 4 below.

TABLE 3

| Therapeutic Product Type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | |
| | Human chorionic gonadotropin | Gonal-F, Follistim |
| | Lutropin-α | Ovidrel |
| | Glucagon | Luveris |
| | Growth hormone releasing hormone (GHRH) | GlcaGen Geref |
| | Secretin | ChiRhoStim (human peptide), SecreFlo (porcine peptide) |
| | Thyroid stimulating hormone (TSH), thyrotropin | Thyrogen |
| Blood Clotting/ Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/Growth factor | Type I alpha-interferon | Infergen |
| | Interferon-αn3 (IFNαn3) | Alferon N |
| | Interferon-β1a (rIFN-β) | Avonex, Rebif |
| | Interferon-β1b (rIFN-β) | Betaseron |
| | Interferon-γ1b (IFN-γ) | Actimmune |
| | Aldesleukin (interleukin 2(IL2), epidermal theymocyte activating factor; ETAF | Proleukin |
| | Palifermin (keratinocyte growth factor; KGF) | Kepivance |
| | Becaplemin (platelet-derived growth factor; PDGF) | Regranex |
| | Anakinra (recombinant IL1 antagonist) | Anril, Kineret |

TABLE 3-continued

| Therapeutic Product Type | Product | Trade Name |
|---|---|---|
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Etanercept (TNF receptor/Fc fusion) | Enbrel |
| | Infliximab (TNFα chimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In another embodiment, the product is a bispecific molecule, e.g., a bispecific antibody. Bispecific molecules, as described herein, include molecules that can bind to two or more distinct antigens or targets. In an embodiment, a bispecific molecule comprises antibody fragments. In one embodiment, the bispecific molecule comprises a bispecific antibody, a bispecific antibody fusion protein, or a bispecific antibody conjugate, a Bi-specific T cell Engager (BiTE) molecule, a Dual Affinity Re-Targeting (DART) Molecule, a Dual Action Fab (DAF) molecule, a nanobody, or other arrangement of antibody fragments resulting in a molecule having the ability to recognize or bind to two distinct antigens.

TABLE 4

Exemplary Products, e.g., Bispecific Molecules

| BsAb (other names, sponsoring organizations) | BsAb format | Targets | Proposed mechanisms of action | Development stages | Diseases (or healthy volunteers) |
|---|---|---|---|---|---|
| Catumaxomab (REMOVAB ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (BLINCYTO ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |

TABLE 4-continued

Exemplary Products, e.g., Bispecific Molecules

| BsAb (other names, sponsoring organizations) | BsAb format | Targets | Proposed mechanisms of action | Development stages | Diseases (or healthy volunteers) |
|---|---|---|---|---|---|
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |

TABLE 4-continued

Exemplary Products, e.g., Bispecific Molecules

| BsAb (other names, sponsoring organizations) | BsAb format | Targets | Proposed mechanisms of action | Development stages | Diseases (or healthy volunteers) |
|---|---|---|---|---|---|
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGFA | Blockade of 2 proangiogenics | Phase I | Solid tumors |
| RG7716 (Roche) | CrossMab | Ang2, VEGFA | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx, | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Cbugai, Roche) | ART-Ig | Factor IXa, factor X | Plasma coagulation | Phase II | Hemophilia |

Other exemplary therapeutic or diagnostic proteins include, but are not limited to any protein described in Tables 1-10 of Leader et al., "Protein therapeutics: a summary and pharmacological classification", Nature Reviews Drug Discovery, 2008, 7:21-39 (incorporated herein by reference); or any conjugate, variant, analog, or functional fragment of the recombinant polypeptides described herein.

Other recombinant products include non-antibody scaffolds or alternative protein scaffolds, such as, but not limited to: DARPins, affibodies and adnectins. Such non-antibody scaffolds or alternative protein scaffolds can be engineered to recognize or bind to one or two, or more, e.g., 1, 2, 3, 4, or 5 or more, different targets or antigens.

Also provided herein are nucleic acids, e.g., exogenous nucleic acids that encode the products, e.g., polypeptides, e.g., recombinant polypeptides described herein. The nucleic acid sequences coding for the desired recombinant polypeptides can be obtained using recombinant methods known in the art, such as, for example by screening libraries from cells expressing the desired nucleic acid sequence, e.g., gene, by deriving the nucleic acid sequence from a vector known to include the same, or by isolating directly from cells and tissues containing the same, using standard techniques. Alternatively, the nucleic acid encoding the recombinant polypeptide can be produced synthetically, rather than cloned. Recombinant DNA techniques and technology are highly advanced and well established in the art. Accordingly, the ordinarily skilled artisan having the knowledge of the amino acid sequence of a recombinant polypeptide described herein can readily envision or generate the nucleic acid sequence that would encode the recombinant polypeptide.

In some embodiments, the exogenous nucleic acid controls the expression of a product that is endogenously expressed by the host cell. In such embodiments, the exogenous nucleic acid comprises one or more nucleic acid sequences that increase the expression of the endogenous product (also referred to herein as "endogenous product transactivation sequence"). For example, the nucleic acid sequence that increases the expression of an endogenous product comprises a constitutively active promoter or a promoter that is stronger, e.g., increases transcription at the desired site, e.g., increases expression of the desired endogenous gene product. After introduction of the exogenous nucleic acid comprising the endogenous product transactivation sequence, said exogenous nucleic acid is integrated into the chromosomal genome of the cell, e.g., at a preselected location proximal to the genomic sequence encoding the endogenous product, such that the endogenous product transactivation sequence increases the transactivation or expression of the desired endogenous product. Other methods for modifying a cell, e.g., introducing an exogenous nucleic acid, for increasing expression of an endogenous product is described, e.g., in U.S. Pat. No. 5,272,071; hereby incorporated by reference in its entirety.

The expression of a product described herein is typically achieved by operably linking a nucleic acid encoding the recombinant polypeptide or portions thereof to a promoter, and incorporating the construct into an expression vector. The vectors can be suitable for replication and integration eukaryotes or prokaryotes. Typical cloning vectors contain other regulatory elements, such as transcription and translation terminators, initiation sequences, and promoters useful for regulation of the expression of the desired nucleic acid sequence.

The nucleic acid sequences described herein encoding a product, e.g., a recombinant polypeptide, or comprising a nucleic acid sequence that can control the expression of an endogenous product, can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors. In embodiments, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193). Vectors derived from viruses are suitable tools to achieve long-term gene transfer since they allow long-term, stable integration of a transgene and its propagation in daughter cells.

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection, e.g., a selection marker or a reporter gene.

In one embodiment, the vector comprising a nucleic acid sequence encoding a polypeptide, e.g., a recombinant polypeptide, further comprises a promoter sequence responsible for the recruitment of polymerase to enable transcription initiation for expression of the polypeptide, e.g., the recombinant polypeptide. In one embodiment, promoter sequences suitable for the methods described herein are usually associated with enhancers to drive high amounts of transcription and hence deliver large copies of the target exogenous mRNA. In an embodiment, the promoter comprises cytomegalovirus (CMV) major immediate early promoters (Xia, Bringmann et al. 2006) and the SV40 promoter (Chernajovsky, Mory et al. 1984), both derived from their namesake viruses or promoters derived therefrom. Several other less common viral promoters have been successfully employed to drive transcription upon inclusion in an expression vector including Rous Sarcoma virus long terminal repeat (RSV-LTR) and Moloney murine leukaemia virus (MoMLV) LTR (Papadakis, Nicklin et al. 2004). In another embodiment, specific endogenous mammalian promoters can be utilized to drive constitutive transcription of a gene of interest (Pontiller, Gross et al. 2008). The CHO specific Chinese Hamster elongation factor 1-alpha (CHEF1α) promoter has provided a high yielding alternative to viral based sequences (Deer, Allison 2004). In addition to promoters, the vectors described herein further comprise an enhancer region as described above; a specific nucleotide motif region, proximal to the core promoter, which can recruit transcription factors to upregulate the rate of transcription (Riethoven 2010). Similar to promoter sequences, these regions are often derived from viruses and are encompassed within the promoter sequence such as hCMV and SV40 enhancer sequences, or may be additionally included such as adenovirus derived sequences (Gaillet, Gilbert et al. 2007).

In one embodiment, the vector comprising a nucleic acid sequence encoding a product, e.g., a polypeptide, e.g., a recombinant polypeptide, described herein further comprises a nucleic acid sequence that encodes a selection marker. In one embodiment, the selectable marker comprises glutamine synthetase (GS); dihydrofolate reductase (DHFR) e.g., an enzyme which confers resistance to methotrexate (MTX); or an antibiotic marker, e.g., an enzyme that confers resistance to an antibiotic such as: hygromycin, neomycin (G418), zeocin, puromycin, or blasticidin. In another embodiment, the selection marker comprises or is compatible with the Selexis selection system (e.g., SUREtechnology Platform™ and Selexis Genetic Elements™, commercially available from Selexis SA) or the Catalant selection system.

In one embodiment, the vector comprising a nucleic acid sequence encoding a recombinant product described herein comprises a selection marker that is useful in identifying a cell or cells comprise the nucleic acid encoding a recombinant product described herein. In another embodiment, the selection marker is useful in identifying a cell or cells that comprise the integration of the nucleic acid sequence encoding the recombinant product into the genome, as described herein. The identification of a cell or cells that have integrated the nucleic acid sequence encoding the recombinant protein can be useful for the selection and engineering of a cell or cell line that stably expresses the product.

Suitable vectors for use are commercially available, and include vectors associated with the GS Expression System™, GS Xceed™ Gene Expression System, or Potelligent® CHOK1SV technology available from Lonza Biologics, Inc, e.g., vectors as described in Fan et al., *Pharm. Bioprocess*. (2013); 1(5):487-502, which is incorporated herein by reference in its entirety. GS expression vectors comprise the GS gene, or a functional fragment thereof (e.g., a GS mini-gene), and one or more, e.g., 1, 2, or 3, or more, highly efficient transcription cassettes for expression of the gene of interest, e.g., a nucleic acid encoding a recombinant polypeptide described herein. A GS mini-gene comprises, e.g., consists of, intron 6 of the genomic CHO GS gene. In one embodiment, a GS vector comprises a GS gene operably linked to a SV40L promoter and one or two polyA signals. In another embodiment, a GS vector comprises a GS gene operably linked to a SV40E promoter, SV40 splicing and polyadenylation signals. In such embodiments, the transcription cassette, e.g., for expression of the gene of interest or recombinant polypeptide described herein, includes the hCMV-MIE promoter and 5' untranslated sequences from the hCMV-MIE gene including the first intron. Other vectors can be constructed based on GS expression vectors, e.g., wherein other selection markers are substituted for the GS gene in the expression vectors described herein.

Vectors suitable for use in the methods described herein include, but are not limited to, other commercially available vectors, such as, pcDNA3.1/Zeo, pcDNA3.1/CAT, pcDNA3.3TOPO (Thermo Fisher, previously Invitrogen); pTarget, HaloTag (Promega); pUC57 (GenScript); pFLAG-CMV (Sigma-Aldrich); pCMV6 (Origene); pEE12 or pEE14 (Lonza Biologics), or pBK-CMV/pCMV-3Tag-7/pCMV-Tag2B (Stratagene).

Cells and Cell Culture

In embodiments, the cell is a mammalian cell. In other embodiments, the cell is a cell other than a mammalian cell. In an embodiment, the cell is a mouse, rat, Chinese hamster, Syrian hamster, monkey, ape, dog, horse, ferret, or cat. In embodiments, the cell is a mammalian cell, e.g., a human cell or a rodent cell, e.g., a hamster cell, a mouse cell, or a rat cell. In another embodiment, the cell is from a duck, parrot, fish, insect, plant, fungus, or yeast. In one embodiment, the cell is an Archaebacteria. In an embodiment, the cell is a species of Actinobacteria, e.g., *Mycobacterium tuberculosis*).

In one embodiment, the cell is a Chinese hamster ovary (CHO) cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1SV GS knockout cell (Lonza Biologics, Inc.). The CHO FUT8 knockout cell is, for example, the Potelligent® CHOK1 SV (Lonza Biologics, Inc.).

In another embodiment, the cell is a Hela, HEK293, HT1080, H9, HepG2, MCF7, Jurkat, NIH3T3, PC12, PER.C6, BHK (baby hamster kidney cell), VERO, SP2/0, NS0, YB2/0, Y0, EB66, C127, L cell, COS, e.g., COS1 and COS7, QC1-3, CHOK1, CHOK1SV, Potelligent CHOK1SV, CHO GS knockout, CHOK1SV GS-KO, CHOS, CHO DG44, CHO DXB11, and CHOZN, or any cells derived therefrom. In one embodiment, the cell is a stem cell. In one embodiment, the cell is a differentiated form of any of the cells described herein. In one embodiment, the cell is a cell derived from any primary cell in culture.

In an embodiment, the cell is any one of the cells described herein that comprises an exogenous nucleic acid encoding a recombinant polypeptide, e.g., expresses a recombinant polypeptide, e.g., a recombinant polypeptide selected from Table 5 or 3.

In an embodiment, the cell culture is carried out as a batch culture, fed-batch culture, draw and fill culture, or a continuous culture. In an embodiment, the cell culture is a suspension culture. In one embodiment, the cell or cell culture is placed in vivo for expression of the recombinant polypeptide, e.g., placed in a model organism or a human subject.

In one embodiment, the culture media is free of serum. Serum-free and protein-free media are commercially available, e.g., Lonza Biologics.

Suitable media and culture methods for mammalian cell lines are well-known in the art, as described in U.S. Pat. No. 5,633,162, for instance. Examples of standard cell culture media for laboratory flask or low density cell culture and being adapted to the needs of particular cell types are for instance: Roswell Park Memorial Institute (RPMI) 1640 medium (Morre, G., The Journal of the American Medical Association, 199, p. 519 f. 1967), L-15 medium (Leibovitz, A. et al., Amer. J. of Hygiene, 78, 1p. 173 ff, 1963), Dulbecco's modified Eagle's medium (DMEM), Eagle's minimal essential medium (MEM), Ham's F12 medium (Ham, R. et al., Proc. Natl. Acad. Sc.53, p 288 ff. 1965) or Iscoves' modified DMEM lacking albumin, transferrin and lecithin (Iscoves et al., J. Exp. med. 1, p. 923 ff., 1978). For instance, Ham's F10 or F12 media were specially designed for CHO cell culture. Other media specially adapted to CHO cell culture are described in EP-481 791. It is known that such culture media can be supplemented with fetal bovine serum (FBS, also called fetal calf serum FCS), the latter providing a natural source of a plethora of hormones and growth factors. The cell culture of mammalian cells is nowadays a routine operation well-described in scientific textbooks and manuals, it is covered in detail e.g. in R. Ian Fresney, Culture of Animal cells, a manual, 4$^{th}$ edition, Wiley-Liss/N.Y., 2000.

Other suitable cultivation methods are known to the skilled artisan and may depend upon the recombinant polypeptide product and the host cell utilized. It is within the skill of an ordinarily skilled artisan to determine or optimize conditions suitable for the expression and production of the recombinant polypeptide to be expressed by the cell.

In one aspect, the cell or cell line comprises an exogenous nucleic acid that encodes a product, e.g., a recombinant polypeptide. In an embodiment, the cell or cell line expresses the product, e.g., a therapeutic or diagnostic product. Methods for genetically modifying or engineering a cell to express a desired polypeptide or protein are well known in the art, and include, for example, transfection, transduction (e.g., viral transduction), or electroporation.

Physical methods for introducing a nucleic acid, e.g., an exogenous nucleic acid or vector described herein, into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

Chemical means for introducing a nucleic acid, e.g., an exogenous nucleic acid or vector described herein, into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In embodiments, the integration of the exogenous nucleic acid into a nucleic acid of the host cell, e.g., the genome or chromosomal nucleic acid of the host cell is desired. Methods for determining whether integration of an exogenous nucleic acid into the genome of the host cell has occurred can include a GS/MSX selection method. The GS/MSX selection method uses complementation of a glutamine auxotrophy by a recombinant GS gene to select for high-level expression of proteins from cells. Briefly, the GS/MSX selection method comprises inclusion of a nucleic acid encoding glutamine synthetase on the vector comprising the exogenous nucleic acid encoding the recombinant polypeptide product. Administration of methionine sulfoximine (MSX) selects cells that have stably integrated into the genome the exogenous nucleic acid encoding both the recombinant polypeptide and GS. As GS can be endogenously expressed by some host cells, e.g., CHO cells, the concentration and duration of selection with MSX can be optimized to identify high producing cells with stable integration of the exogenous nucleic acid encoding the recombinant polypeptide product into the host genome. The GS selection and systems thereof is further described in Fan et al., *Pharm. Bioprocess.* (2013); 1(5):487-502, which is incorporated herein by reference in its entirety.

Other methods for identifying and selecting cells that have stably integrated the exogenous nucleic acid into the host cell genome can include, but are not limited to, inclusion of a reporter gene on the exogenous nucleic acid and assessment of the presence of the reporter gene in the cell, and PCR analysis and detection of the exogenous nucleic acid.

In one embodiment, the cells selected, identified, or generated using the methods described herein are capable of producing higher yields of protein product than cells that are selected using only a selection method for the stable expression, e.g., integration of exogenous nucleic acid encoding the recombinant polypeptide. In an embodiment, the cells selected, identified, or generated using the methods described herein produce 2-fold, 3-fold, 4-fold, 5-fold, 6-fold, 7-fold, 8-fold, 9-fold, or 10-fold or more of the product, e.g., recombinant polypeptide, as compared to cells that were not contacted with an inhibitor of protein degradation, or cells that were only selected for stable expression, e.g., integration, of the exogenous nucleic acid encoding the recombinant polypeptide.

Methods for Cell Line and Recombinant Polypeptide Production

The current state of the art in both mammalian and microbial selection systems is to apply selective pressure at the level of the transcription of DNA into RNA. The gene of interest is tightly linked to the selection marker making a high level of expression of the selective marker likely to result in the high expression of the gene of interest. Cells which express the selection marker at high levels are able to survive and proliferate, those which do not are less likely to survive and proliferate, e.g., apoptose and/or die. In this way a population of cells can be enriched for cells expressing the selection marker and by implication the gene of interest at high levels. This method has proved very successful for expressing straightforward proteins. In embodiments, the process described herein provides a substantially pure protein product. As used herein, "substantially pure" is meant substantially free of pyrogenic materials, substantially free of nucleic acids, and/or substantially free of endogenous cellular proteins enzymes and components from the host cell, such as polymerases, ribosomal proteins, and chaperone proteins. A substantially pure protein product contains, for example, less than 25%, 20%, 15%, 10%, 9%, 8%, 7%, 6%, 5%, 4%, 3%, 2%, or 1% of contaminating endogenous protein, nucleic acid, or other macromolecule from the host cell.

The methods and systems can be used with methods for recovering and purifying products that are well established in the art. For recovering the recombinant polypeptide product, a physical or chemical or physical-chemical method is used. The physical or chemical or physical-chemical method can be a filtering method, a centrifugation method, an ultracentrifugation method, an extraction method, a lyophilization method, a precipitation method, a crystallization method, a chromatography method or a combination of two or more methods thereof. In an embodiment, the chromatography method comprises one or more of size-exclusion chromatography (or gel filtration), ion exchange chromatography, e.g., anion or cation exchange chromatography, affinity chromatography, hydrophobic interaction chromatography, and/or multimodal chromatography.

The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesised by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316 L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBv13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, North Carolina, USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri,* and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorphs, Yarrowia lipolytic* a, or *Schizosaccharomyces pombe.* Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora, Bacillariophyceae, Dunaliella, Chlorella, Chlamydomonas, Cyanophyta* (cyanobacteria), *Nannochloropsis, Spirulina,* or *Ochromonas*), or a plant cell (e.g., cells from monocotyledonous plants (e.g., maize, rice, wheat, or Setaria), or from a dicotyledonous plants (e.g., cassava, potato, soybean, tomato, tobacco, alfalfa, *Physcomitrella patens* or Arabidopsis).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus*. *Bacillus* that can be used is, e.g. the *B. subtilis, B. amyloliquefaciens, B. licheniformis, B. natto,* or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West 12$^{th}$ Avenue, Columbus OH 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-nl, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, S pneumoniae pediatric vaccine, malaria vaccine, Neisseria meningitidis Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™) bevacizumab (AVASTIN™), trastuzumab (HERCEPTIN™), pegrilgrastim (NEULASTA™), or any other suitable polypeptide including biosimilars and biobetters.

Other suitable polypeptides are those listed below in Table 5, and in Table 1 of US2016/0097074.

TABLE 5

| Protein Product | Reference Listed Drug |
|---|---|
| interferon gamma-1b | ACTIMMUNE ® |
| alteplase; tissue plasminogen activator | ACTIVASE ®/ CATHFLO ® |
| Recombinant antihemophilic factor | ADVATE |
| human albumin | ALBUTEIN ® |
| Laronidase | ALDURAZYME ® |
| Interferon alfa-N3, human leukocyte derived | ALFERON N ® |
| human antihemophilic factor | ALPHANATE ® |
| virus-filtered human coagulation factor IX | ALPHANINE ® SD |
| Alefacept; recombinant, dimeric fusion protein LFA3-Ig | AMEVIVE ® |
| Bivalirudin | ANGIOMAX ® |
| darbepoetin alfa | ARANESP ™ |
| Bevacizumab | AVASTIN ™ |
| interferon beta-1a; recombinant | AVONEX ® |
| coagulation factor IX | BENEFIX ™ |
| Interferon beta-1b | BETASERON ® |
| Tositumomab | BEXXAR ® |
| antihemophilic factor | BIOCLATE ™ |
| human growth hormone | BIOTROPIN ™ |
| botulinum toxin type A | BOTOX ® |
| Alemtuzumab | CAMPATH ® |
| acritumomab; technetium-99 labeled | CEA-SCAN ® |
| alglucerase; modified form of beta-glucocerebrosidase | CEREDASE ® |
| imiglucerase; recombinant form of beta-glucocerebrosidase | CEREZYME ® |
| crotalidae polyvalent immune Fab, ovine | CROFAB ™ |
| digoxin immune fab [ovine] | DIGIFAB ™ |
| Rasburicase | ELITEK ® |
| Etanercept | ENBREL ® |
| epoietin alfa | EPOGEN ® |
| Cetuximab | ERBITUX ™ |
| algasidase beta | FABRAZYME ® |

TABLE 5-continued

| Protein Product | Reference Listed Drug |
| --- | --- |
| Urofollitropin | FERTINEX ™ |
| follitropin beta | FOLLISTIM ™ |
| Teriparatide | FORTEO ® |
| human somatropin | GENOTROPIN ® |
| Glucagon | GLUCAGEN ® |
| follitropin alfa | GONAL-F ® |
| antihemophilic factor | HELIXATE ® |
| Antihemophilic Factor; Factor XIII | HEMOFIL |
| adefovir dipivoxil | HEPSERA ™ |
| Trastuzumab | HERCEPTIN ® |
| Insulin | HUMALOG ® |
| antihemophilic factor/von Willebrand factor complex-human | HUMATE-P ® |
| Somatotropin | HUMATROPE ® |
| Adalimumab | HUMIRA ™ |
| human insulin | HUMULIN ® |
| recombinant human hyaluronidase | HYLENEX ™ |
| interferon alfacon-1 | INFERGEN ® |
| eptifibatide | INTEGRILIN ™ |
| alpha-interferon | INTRON A ® |
| Palifermin | KEPIVANCE |
| Anakinra | KINERET ™ |
| antihemophilic factor | KOGENATE ®FS |
| insulin glargine | LANTUS ® |
| granulocyte macrophage colony-stimulating factor | LEUKINE ®/ LEUKINE ® LIQUID |
| lutropin alfa for injection | LUVERIS |
| OspA lipoprotein | LYMERIX ™ |
| Ranibizumab | LUCENTIS ® |
| gemtuzumab ozogamicin | MYLOTARG ™ |
| Galsulfase | NAGLAZYME ™ |
| Nesiritide | NATRECOR ® |
| Pegfilgrastim | NEULASTA ™ |
| Oprelvekin | NEUMEGA ® |
| Filgrastim | NEUPOGEN ® |
| Fanolesomab | NEUTROSPEC ™ (FORMERLY LEUTECH ®) |
| somatropin [rDNA] | NORDITROPIN ®/ NORDITROPIN NORDIFLEX ® |
| Mitoxantrone | NOVANTRONE ® |
| insulin; zinc suspension; | NOVOLIN L ® |
| insulin; isophane suspension | NOVOLIN N ® |
| insulin, regular; | NOVOLIN R ® |
| Insulin | NOVOLIN ® |
| coagulation factor VIIa | NOVO SEVEN ® |
| Somatropin | NUTROPIN ® |
| immunoglobulin intravenous | OCTAGAM ® |
| PEG-L-asparaginase | ONCASPAR ® |
| abatacept, fully human soluable fusion protein | ORENCIA ™ |
| muromomab-CD3 | ORTHOCLONE OKT3 ® |
| high-molecular weight hyaluronan | ORTHOVISC ® |
| hunan chorionic gonadotropin | OVIDREL ® |
| live attenuated Bacillus Calmette-Guerin | PACIS ® |
| peginterferon alfa-2a | PEGASYS ® |
| pegylated version of interferon alfa-2b | PEG-INTRON ™ |
| Abarelix (injectable suspension); gonadotropin-releasing hormone antagonist | PLENAXIS ™ |
| epoietin alfa | PROCRIT ® |
| Aldesleukin | PROLEUKIN, IL-2 ® |
| Somatrem | PROTROPIN ® |
| dornase alfa | PULMOZYME ® |
| Efalizumab; selective, reversible T-cell blocker | RAPTIVA ™ |
| combination of ribavirin and alpha interferon | REBETRON ™ |
| Interferon beta 1a | REBIF ® |
| antihemophilic factor | RECOMBINATE ® RAHF/ |
| antihemophilic factor | REFACTO ® |
| Lepirudin | REFLUDAN ® |
| Infliximab | REMICADE ® |
| Abciximab | REOPRO ™ |
| Reteplase | RETAVASE ™ |
| Rituxima | RITUXAN ™ |
| interferon alfa-2$^a$ | ROFERON-A ® |
| Somatropin | SAIZEN ® |

TABLE 5-continued

| Protein Product | Reference Listed Drug |
| --- | --- |
| synthetic porcine secretin | SECREFLO ™ |
| Basiliximab | SIMULECT ® |
| Eculizumab | SOLIRIS ® |
| Pegvisomant | SOMAVERT ® |
| Palivizumab; recombinantly produced, humanized mAb | SYNAGIS ™ |
| thyrotropin alfa | THYROGE ® |
| Tenecteplase | TNKASE ™ |
| Natalizumab | TYSABRI ® |
| human immune globulin intravenous 5% and 10% solutions | VENOGLOBULIN-S ® |
| interferon alfa-n1, lymphoblastoid | WELLFERON ® |
| drotrecogin alfa | XIGRIS ™ |
| Omalizumab; recombinant DNA-derived humanized monoclonal antibody targeting immunoglobulin-E | XOLAIR ® |
| Daclizumab | ZENAPAX ® |
| ibriturnomab tiuxetan | ZEVALIN ™ |
| Somatotropin | ZORBTIVE ™ (SEROSTIM ®) |

In embodiments, the polypeptide is a hormone, blood clotting/coagulation factor, cytokine/growth factor, antibody molecule, fusion protein, protein vaccine, or peptide as shown in Table 3.

In embodiments, the protein is multispecific protein, e.g., a bispecific antibody as shown in Table 4.

EXAMPLES

The system and method of the present disclosure are further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples specifically point out various aspects of the present disclosure, and are not to be construed as limiting in any way the remainder of the disclosure.

Example 1. Processing Solution Components for Processing a Bioproduct According to the Disclosure Tables 6-9 list the components, ingredient concentrations and buffer requirements of a processing solution according to the disclosure for one biologic prepared in a bioreactor. Buffers A-L in Tables 7-9 correspond to Buffers A-L identified in Table 6.

The bioprocess container can be used to contain the following buffers: Tris, Tris-Base, Tricine, HEPES, MOPS, PIPES, TAPS, bicine, BES, TES, cacodylate, MES, acetate, MKP, ADA, ACES, glycinamide, acetamidoglycine, acetic acid, citric acid, glycine, glycine glycinate, sodium phosphate, ethanol, hydrochloric acid, sodium hydroxide, guanidinium chloride, guanidine hydrochloride, sodium chloride, or a combination of any of these buffers or other buffers.

Tris is also known as tris(hydroxymethyl)aminomethane. HEPES is also known as 4-(2-hydroxyethyl)-1-piperazineethanesulfonic acid. Tris-Base is also known as 2-Amino-2-(hydroxymethyl)-1,3-propanediol, THAM, Tris base, and Tris(hydroxymethyl)aminomethane, Trometamol. MOPS is also known as 3-(N-morpholino)propanesulfonic acid. PIPES is also known as piperazine-N,N'-bis(2-ethanesulfonic acid). TAPS is also known as [tris(hydroxymethyl)methylamino]propanesulfonic acid. BES is also known as N,N-Bis(2-hydroxyethyl)-2-aminoethanesulfonic acid, N,N-Bis(2-hydroxyethyl)taurine. TES is also known as 2-[(2-Hydroxy-1,1-bis(hydroxymethyl)ethyl)amino]ethanesulfonic acid, N-[Tris(hydroxymethyl)methyl]-2-aminoethanesulfonic acid, and TES free acid. MES is also known as 2-(N-morpholino)ethanesulfonic acid. MKP is also known as Monopotassium phosphate. ADA is also known as N-(2-Acetamido)iminodiacetic acid, N-(Carbamoylmethyl)iminodiacetic acid. ACES is also known as N-(2-Acetamido)-2-aminoethanesulfonic acid.

TABLE 6

| Code | Buffer | Total Volume (1X) | Number of 2000 L bags | Max Conc Factor (capped at 10X) | Volume After Concentration | Number of 2000 L Bags for Concentrate |
|---|---|---|---|---|---|---|
| Buffer A | 6M Gua-HCl | 8,534 | 5 | 1 | 8534 | 9 |
| Buffer B | 0.1M Acetic Acid, 18% EtOH | 8,534 | 5 | 1 | 8534 | 9 |
| Buffer C | 50 mM Glycine Glycinate, 250 mM NaCl (pH 8.0) | 38,581 | 20 | 8 | 4823 | 5 |
| Buffer D | 0.1M Glycine, 0.1M NaCl (pH 3.5) | 14,935 | 8 | 10 | 1494 | 2 |
| Buffer E | 0.1M Citric Acid pH 2.1 | 6,401 | 4 | 10 | 640 | 1 |
| Buffer F | 18% Ethanol | 800 | 1 | 1 | 800 | 1 |
| Buffer G | 1M HCl | 30 | 1 | 1 | 30 | 1 |
| Buffer H | 1M Tris-Base | 49 | 1 | 1 | 49 | 1 |
| Buffer I | 20 mM Na-phosphate, 80 mM NaCl (pH 6.5) | 19,127 | 10 | 10 | 1913 | 2 |
| Buffer J | 0.1M NaOH | 13,577 | 7 | 10 | 1358 | 2 |
| Buffer K | 20 mM Na-phosphate, 2M NaCl (pH 6.5) | 3,556 | 2 | 1 | 3556 | 4 |
| Buffer L | 0.01M NaOH | 2,546 | 2 | 10 | 255 | 1 |

TABLE 7

| Buffer Components | Component 1 | Mass component 1 (g/L) | Total Mass Component 1 (g) |
|---|---|---|---|
| Buffer A | Guanidine hydrochloride | 573 | 4890168.19 |
| Buffer B | Glacial acetic acid | 6.50 | 55473.1121 |
| Buffer C | Glycine USP | 7.20 | 138891.1716 |
| Buffer D | Glycine USP | 7.50 | 112013.0148 |
| Buffer E | Citric acid monohydrate | 20.79 | 133071.4616 |
| Buffer F | Ethanol absolute | 145.00 | 116013.4796 |
| Buffer G | Hydrochloric acid 2.0N solution | 515.00 | 15602.87957 |
| Buffer H | Tromethamine | 117.57 | 5727.69772 |
| Buffer I | Sodium phosphate monobasic monohydrate | 1.84 | 35193.05152 |
| Buffer J | sodium hydroxide pellets | 4.00 | 54309.34052 |
| Buffer K | Sodium phosphate monobasic monohydrate | 0.51 | 1813.54405 |
| Buffer L | sodium hydroxide pellets | 0.40 | 1018.300135 |

TABLE 8

| Buffer Components | Component 2 | Mass component 2 (g/L) | Total Mass Component 2 (g) |
|---|---|---|---|
| Buffer A | | | |
| Buffer B | Ethanol Absolute | 145 | 1237477.116 |
| Buffer C | Glycine sodium salt hydrate | 0.28 | 5401.323339 |
| Buffer D | Sodium Chloride | 5.84 | 87220.80088 |
| Buffer E | | | |
| Buffer F | | | |
| Buffer G | | | |
| Buffer H | | | |
| Buffer I | Sodium phosphate dibasic heptahydrate | 1.79 | 34236.71859 |
| Buffer J | Sodium hydroxide 50% solution | 5.22 | 70873.68938 |
| Buffer K | Sodium phosphate dibasic heptahydrate | 3.97 | 14117.19584 |
| Buffer L | Sodium hydroxide 50% solution | 0.523 | 1331.427426 |

TABLE 9

| Buffer Components | Component 3 | Mass component 3 (g/L) | Total Mass Component 3(g) |
|---|---|---|---|
| Buffer A | | | |
| Buffer B | | | |
| Buffer C | Sodium chloride | 29.1 | 561352 |
| Buffer D | Hydrochloric acid | as required | |
| Buffer E | | | |

TABLE 9-continued

| Buffer Components | Component 3 | Mass component 3 (g/L) | Total Mass Component 3(g) |
|---|---|---|---|
| Buffer F | | | |
| Buffer G | | | |
| Buffer H | | | |
| Buffer I | Sodium chloride | 4.68 | 89512.76146 |
| Buffer J | | | |
| Buffer K | Sodium chloride | 108.22 | 384827 |
| Buffer L | | | |

The disclosure will be further illustrated in the following claims.

What is claimed is:

1. A system for delivering a processing solution, the system comprising:
a bioprocess container containing a concentrated processing solution, the bioprocess container having an inner layer for contacting the concentrated processing solution and an outer layer configured to support the inner layer, the bioprocess container configured to contain the concentrated processing solution when the bioprocess container is transported from a first site to a second site;
a processing area having at least one processing unit at the second site different from the first site; and
a pipe connecting the bioprocess container to the at least one processing unit at the second site, the pipe having a valve to:
allow the concentrated processing solution to flow from the bioprocess container to the at least one processing unit to combine the concentrated processing solution with a biopolymer containing solution produced in the at least one processing unit, and
maintain a sterile condition of the processing unit when the bioprocess container is disconnected from the pipe,
wherein the processing solution is at least one of a buffer and media.

2. The system of claim 1, further comprising a controller connected to the at least one processing unit, wherein the concentrated processing solution is provided based on a determination by the controller that the processing solution is required when the determination is communicated from the second site to the first site.

3. The system of claim 1, wherein the system is configured to dilute the concentrated processing solution prior to combining with the biopolymer containing solution.

4. The system of claim 1, further comprising a controller configured to determine a bioburden of the processing solution.

5. The system of claim 1, comprising a dilution liquid supply, wherein the concentrated processing solution from the bioprocess container and at least one of water and buffer from the dilution liquid supply is added to an inlet of an inline processing solution dilution system to result in a diluted processing solution.

6. The system of claim 1, wherein the processing solution is one of Tris, Tris-Base, Tricine, HEPES, MOPS, PIPES, TAPS, bicine, BES, TES, cacodylate, MES, acetate, MKP, ADA, ACES, glycinamide, acetamidoglycine, acetic acid, citric acid, glycine, glycine glycinate, sodium phosphate, ethanol, hydrochloric acid, sodium hydroxide, guanidinium chloride, guanidine hydrochloride, sodium chloride, and a combination of any of these.

7. A pharmaceutical production facility comprising:
at least one bioprocess container having an inner layer for contacting a concentrated processing solution and an outer layer configured to support the inner layer, the at least one bioprocess container configured to contain the concentrated processing solution when the at least one bioprocess container is transported from a first site to a second site;
a buffer storage area capable of receiving the at least one bioprocess container;
a processing area having at least one processing unit;
a wall separating the buffer storage area from the processing area; and
at least one pipe having a first end in the buffer storage area and a second end in the processing area, the first end configured to connect to the at least one bioprocess container and the second end configured to connect to the at least one processing unit,
wherein the at least one pipe has a valve to maintain a sterile condition of the at least one processing unit when the at least one bioprocess container is disconnected from the at least one pipe.

8. The pharmaceutical production facility of claim 7, further comprising:
a platform in the buffer storage area, the platform being configured to support the at least one bioprocess container, the at least one bioprocess container including a plurality of bioprocess containers, the platform having a first level configured to support at least one bioprocess container of the plurality of bioprocess containers and a second level configured to support at least one bioprocess container of the plurality of bioprocess containers,
wherein the platform is configured to allow a user to place a bioprocess container of the plurality of bioprocess containers onto the platform using a forklift, and the platform being configured to allow a user to remove the respective bioprocess container from the platform using the forklift.

9. The pharmaceutical production facility of claim 8, further comprising a plurality of inlets spaced apart along the platform, each inlet being connected to the at least one pipe, and each inlet being configured to be connected to an outlet of a bioprocess container of the plurality of bioprocess containers, wherein the processing area is configured as a cleanroom environment.

10. The pharmaceutical production facility of claim 7, wherein the valve is positioned within or adjacent to the wall separating the buffer storage area from the processing area.

* * * * *